US005464932A

United States Patent [19]
Allcock et al.

[11] Patent Number: 5,464,932
[45] Date of Patent: Nov. 7, 1995

[54] PHOTOCROSSLINKABLE POLYPHOSPHAZENES AND THEIR USE AS MICROENCAPSULATION MATERIALS

[75] Inventors: Harry R. Allcock; Charles G. Cameron; Dawn E. Smith, all of State College, Pa.

[73] Assignee: The Penn State Research Foundation, University Park, Pa.

[21] Appl. No.: 228,574

[22] Filed: Apr. 15, 1994

[51] Int. Cl.⁶ .................................................. C08G 79/02
[52] U.S. Cl. .......................... 528/399; 524/600; 524/606; 524/608; 528/168; 528/169
[58] Field of Search .................................. 524/600, 606, 524/608; 528/168, 169, 399

[56] References Cited

U.S. PATENT DOCUMENTS

| | | | |
|---|---|---|---|
| 2,690,966 | 10/1954 | Minsk et al. | 430/287 |
| 4,278,660 | 7/1981 | Allcock et al. | 424/78 |
| 4,440,921 | 4/1984 | Allcock et al. | 528/168 |
| 4,451,647 | 5/1984 | Allcock et al. | 536/21 |
| 4,880,622 | 11/1989 | Allcock et al. | 424/78 |
| 5,053,451 | 10/1991 | Allcock et al. | 524/600 |
| 5,149,543 | 9/1992 | Cohen et al. | 424/499 |
| 5,248,585 | 9/1993 | Lynch et al. | 430/326 |

OTHER PUBLICATIONS

Allcock, H. A. et al. "Synthesis and Characgerization of Photo–Cross–Linkable Small–Molecule and High–Polymeric Phosphazenes Bearing Cinnamate Groups," *Macromolecules* 1994, 27, 3125–3130 (Abstract published in *Advance ACS Abstracts*, May 1, 1994).

Allcock, H. A. et al., "Synthesis of Photo–Cross–Linkable Chalcone–Bearing Polyphosphazenes," *Macromolecules*, 1994, 27, 3131–3135 (Abstract published in *Advance ACS Abstracts*, May 1, 1994).

Allcock, H. A. et al., "Activity of Urea Amidohydrolase Immobilized within Poly[di(methoxyethoxyethoxy)phosphazene] Hydrogels," *Biomaterials*, 1994, 15(7), 502–506.

Akelah, A., et al., "Photochemical Reactions of Polymers Bearing Chalcone Residues," *Polym. Int.* 1992, 28, 307–312.

Allcock, H. R. and Kugel, R. L., "Synthesis of High Polymeric Alkoxy–and Aryloxyphosphonitriles," *J. Am. Chem. Soc.* 1965, 87, 4216–4217.

Allcock, H. R. and Kugel, R. L., "Ionic Polymerization of Diphenylvinylphosphine Oxide," *J. Polymer Sci., Part A* 1963, 1 3627–3642.

Allcock, H. R., "New Reactions of Phosphonitrilic Chloride Trimer. Substitution and Cleavage Reactions with Catechol and Triethylamine," *J. Am. Chem. Soc.* 1963, 85, 4050–4051.

Allcock, H. R., "Phosphonitrilic Compounds. II. Reactions of Phosphonitrilic Chlorides with Cathechol and Triethylamine," *J. Am. Chem. Soc.* 1964, 86, 2591–2595.

Allcock, H. R. "X–Ray Induced Polymerization of Diphenylvinyl Phosphine Oxide," *J. Polymer Sci., Part A*, 1964, 2, 4087–4095.

(List continued on next page.)

*Primary Examiner*—Shelley A. Dodson
*Attorney, Agent, or Firm*—Cheryl K. Zalesky; Kilpatrick & Cody

[57] ABSTRACT

Chalcone and cinnamate bearing polyphosphazenes are disclosed. The polyphusphazenes contain a sufficient number of chalcone or cinnamate groups, or a combination thereof, to achieve a photocrosslinkable material. The phosphazene backbone is transparent from the near and mid-UV to the near infrared region, minimizing degradation of the skeleton both under the high intensity UV irradiation required for the photo-crosslinking reaction and during subsequent exposure to light disclosed. These photosensitive polyphosphazenes are useful for a variety of purposes, including in photolithography, photocurable coatings, for the stabilization of certain non-linear optical properties, and for use in the construction of biocompatible semi-permeable membranes which can be used to encapsulate living cells or other substances of implantation.

30 Claims, 3 Drawing Sheets

OTHER PUBLICATIONS

Allcock, H. R., and Siegel, L. A., "Phosphonitrilic Compounds. III. Molecular Inclusion Compounds of Tris(o–phenylenedioxy)–phosphonitrile Trimer," *J. Am Chem. Soc.* 1964, 86, 5140–5144.

Allcock, H. R., et al., "Phosphonitrilic Compounds. IV. Preparation and Polymerization of Allylaminophosphonitrile Compounds," *J. Org. Chem.* 1965, 30, 947–949.

Allcock, H. R., and Kugel, R. L., "Synthesis of High Polymeric Alkoxy– and Aryloxyphosphonitriles" *J. Am. Chem. Soc.* 1965, 87, 4216–4217.

Allcock, H. R., and Kugel, R. L., "Phosphonitrilic Compounds. V. Cyclized Products From the Reactions of Hexachlorocyclotriphosphazene (Phosphonitrilic Chloride Trimer) with Aromatic Dihydroxy, Dithiol, and Diamino Compounds," *Inorg. Chem.* 1966, 5(6) 1016–1020.

Allcock, H. R., et al., "Phosphonitrilic Compounds. VI. High Molecular Weight Poly(alkoxy– and aryloxyphosphazenes)," *Inorg. Chem.* 1968, 5(10), 1709–1715.

Allcock, H. R., and Kugel, R. L., "Phosphonitrilic Compounds. VII. High Molecular Weight Poly(diaminophosphazenes)," *Inorg. Chem.* 1966, 5(10), 1716–1718.

Allcock, H. R., "Phosphonitrilic Chemistry," *Chem. and Eng. News* 1968, 46, 68–81.

Allcock, H. R., and Kugel, R. L., "Degradation of Halogenophosphazenes to a New Phosphorane System," *J. Chem. Soc., Chem. Commun.* 1968, 24, 1606–1607.

Allcock, H. R., "Phosphonitrilic Polymers," *Encyclopedia of Polymer Sci. and Techn.* 1969, 10, 139–144.

Allcock, H. R., and Birdsall, W. J., "Phosphonitric Radical Anions," *J. Am. Chem. Soc.* 1969, 91, 7541–7542.

Allcock, H. R., et al., "Ligand Exchange with Organophosphazenes," *J. Chem. Soc., Chem. Commun.* 1970, 20, 1283–1284.

Allcock, H. R., and Moore, G. Y., "Synthesis of Poly(organophosphazene) Copolymers and Cross–linked Polymers by Ligand Exchange," *Macromolecules* 1972, 5, 231–232.

Allcock, H. R., "Recent Advances in Phosphazene (Phosphonitrilic) Chemistry," *Chem. Rev.* 1972, 72, 315–356.

Allcock, H. R., et al., "Phosphonitrilic Compounds. XV. High Molecular Weight Poly[bis(amino)phosphazenes] and Mixed–Substituent Poly(aminophosphazenes)," *Inorg. Chem.* 1972, 11(7), 2584–2590.

Allcock, H. R., "Inorganic Polymers," *Scientific American*, Mar. 1974, pp. 66–74.

Allcock, H. R., and Moore, G. Y., "Polymerization and Copolymerization of Phenylhalogenocyclotriphosphazenes," *Macromolecules* 1975, 8(4), 377–382.

Allcock, H. R., "Poly(organophosphazenes), The First Technologically useful inorganic Polymers Since the Silicones" *Chem. Tech.* 1975, 5, 552–560.

Allcock, H. R., "Polyphosphazenes: New Polymers with Inorganic Backbone Atoms," *Science* 1976, 193, 1214–1219.

Allcock, H. R., "A New Route for Poly(organophosphazene) Synthesis, Polyermization, Copolymerization, and Ring–Ring Equilibration of Trifluoroethoxy–and Chloro–substituted Cyclotriphosphazenes," *Macromolecules* 1978, 11(1), 179–186.

Allcock, H. R., "Poly(organophosphazenes) Designed for Biomedical Uses," *Organometallic Polymers*, Academic Press, 1978, 283–288.

Allcock, H. R., "Polymerization of Cyclic Phosphazenes," *Polymer* 1980, 21, 673–683.

Allcock, H. R., "Synthesis of Alkylphosphazene High Polymers via the Polymerization of Monoalkylpentachloro–cyclotriphosphazenes," *Macromolecules* 1980, 13, 1332–1338.

Allcock, H. R. and Fuller, T. J., "Phosphazene High Polyers with Steroidal Side Groups," *Macromolecules* 1980, 13, 1338–1345.

Allcock, H. R., et al., "Reactions of Steroid Salts with Hexachlorocyclotri–phosphazene," *J. Org. Chem.* 1981, 46, 13–22.

Allcock, H. R., "Controlled Sythesis of Organic/Inorganic Polymers that Possess a Backbone of Phosphorus and Nitrogen Atoms," *Makromol. Chem.* (*Proc. IUPAC Conf. on Macromolecules, Florence, Italy, 1980*) Suppl. 4, 3–19.

Allcock, H. R., and Harris, P. J., "Synthesis of New 1–Halo–1–alkyltetrachlorocyclo–triphosphazenes, including the First Cyclophosphazenes with a P–I Bond," *Inorg. Chem* 1981, 20, 2844–2848.

Allcock, H. R., "Phosphazene Rings and High Polymers Linked to Transition Metals or Biologically Active Organic Species," *ACS Symp. Ser.* (*Proc. of Int. Conf. on Phosphorus Chemistry, Durham, N.C. 1981*), 1981, 171, 311–314.

Allcock, H. R. et al., "Hydrolysis Pathways for Aminophosphazenes," *Inorg. Chem.* 1982, 21, 515–521.

Allcock, H. R., et al., "Phosphazene High Polymer with Bioactive Substituent Groups: Prospective Anesthetic Aminophosphazenes," *Macromolecules* 1982, 15(3), 689–693.

Allcock, H. R., et al., "Coupling of Cyclic and High–Polymeric [(Aminoaryl)oxy]phosphazenes to Carboxylic Acids: Prototypes for Bioactive Polymers," *Macromolecules* 1982, 15, 693–696.

Allcock, H. R., et al., "Phosphazenes with Olefinic Side Groups: Proton Abstraction Reactions of Fluoroalkoxy Derivatives," *Organometallics* 1982, 1, 1443–1449.

Allcock, H. R. and Scopelianos, A. G., "Synthesis of Sugar–Substituted Cyclic and Polymeric Phosphazenes, and their Oxidation, Reduction, and Acetylation Reactions," *Macromolecules* 1983, 16, 715–719.

Allcock, H. R., et al., "Synthesis of 1–Halo– and 1–Alkyl–1–phenyltetrachlorocyclotriphosphazene Polymerization Monomers from Bi(cyclophosphazenes)," *Organometallics* 1983, 2, 1514–1523.

Allcock, H. R., "Cyclic and High–Polymeric Phosphazenes as Carrier Molecules for Carboranyl, Metallo, or Bioactive Organic Side Groups," Chapter in Rings, Clusters, and Polymers of the Main Group Elements, *ACS Symp. Ser.* 1983, 232, 49–67.

Allcock, H. R., "Reactions of Organometallic Reagents With Halogenophosphazene Cyclic Trimers, Tetramers, and High Polymers," *Phosphorus and Sulfur*, 1983, 18, 267–270.

Allcock, H. R., "A New Approach to Polymer Chenistry: Organometallic and Bioactive Phosphazenes," *J. Poly. Sci., Polym. Symp.* 1983, 70, 71–77.

Allcock, H. R., et al., "Reactions between Hexachlorocyclotri–phosphazene and Hexamethylcyclotrisiloxane: Polymerization, Ring Cleavage, and Cross–linking," *Macromolecules*, 1985, 18, 139–144.

Allcock, H. R., "Inorganic Macromolecules: Developments at the Interface of Inorganic, Organic, and Polymer Chenistry," *Chem. and Eng. News*, 1985, 63, 22–36.

Allcock, H. R., et al., "Polyphosphazenes with Etheric Side Groups: Prospective Biomedical and Solid Electrolyte Polymers," *Macromolecules* 1986, 19, 1508–1512.

Allcock, H. R. and Kwon, S., "Covalent Linkage of Proteins to Surface–Modified Poly(organophosphazenes): Immobilization of Glucose–6–Phosphate Dehydrogenase and Trypsin," *Macromolecules* 1986, 19, 1502–1508.

Allcock, H. R., "Polyphosphazenes," Chapter in *Encyclopedia of Polymer Science and Engineering* (Mark, Bikales, Overberger, Menges, Eds.) John Wiley & Sons: New York 1988, 13, 2d Ed., 31–41.

Allcock, H. R., "Phosphazene High Polymers," Chapter in *Comprehensive Polymer Science*, (G. C. Eastmond, A. Ledwith, S. Russo, and P. Sigwalt, eds.), Pergamon Press: Oxford, vol. 4, 1989, 525–532.

Allcock, H. R., et al., "Effects of Organic Side Group Structures on the Properties of Poly(organophosphazenes)," *Macromolecules* 1988, 21, 323–334.

Allcock, H. R., "The Current Status of Polyphosphazene Chemistry," Chapter in *Inorganic and Organometallic Polymers*, (Zeldin, M.; Wynne, K. J.; Allcock, H. R.; eds.) ACS *Symp. Ser 360*, 1988, 250–267.

Allcock, H. R., et al., "Amphiphilic Polyphosphazenes as Membrane Materials: Influence of Side Group on Radiation Cross–linking" *Biomaterials* 1988, 9, 500–508.

Allcock, H. R., et al., "Hydrophilic Polyphosphazenes as Hydrogels: Radiation Cross–linking and Hydrogel Characteristics of Poly[bis(methoxyethoxyethoxy)phosphazene]," *Biomaterials* 1988, 9, 509–513.

Allcock, H. R. and Kwon, S., "An Ionically Cross–linkable Polyphosphazene: Poly[bis(carboxylatophenoxy)phosphazene] and its Hydrogels and Membranes," *Macromolecules* 1989, 22, 75–79.

Allcock, H. R., "Reactions of Inorganic High Polymers as a Route to Tailored Solids," *Proc. of 11th Int. Symp. on Reactive Solids*, Princeton, 1988, *Solid State Ionics* 1989, 32/33, 761–764.

Allcock, H. R., "Organometallic and Bioactive Cyclophosphazenes, and the Relationship to Inorganic Macromolecules," Proc. of Int. Symp. on Inorg. Ring Systems, Amherst, Mass., *Phosphorus, Sulfur, and Silica*, 1989, 41, 119–133.

Allcock, H. R., "Polyphosphazenes as New Biomedical and Bioactive Materials," Chapter in *Biodegradable Polymers as Drug Delivery Systems*, (R. Langer and M. Chasin, eds), Marcel Dekker: New York 1990, 163–193.

Allcock, H. R., "Chemical Synthesis at the Boundary Between Polymer Chemistry and Inorganic Materials," *The Chemist*, 1990, 10–16.

Allcock, H. R., et al., "Ring–Opening Polymerization of Phosphazenes: Mechanism and Idiosyncrasies," *Polym. Prepr.* (Amer. Chem. Soc., Div. Polym. Chem.) 1990, 31, 48–50.

Allcock, H. R. and Chang, J. Y., "Poly(organophosphazenes) with Oligopeptides as Side Groups: Prospective Biomaterials", *Macromolecules* 1991, 24, 993–999. Allcock H. R., "Organometallic and Bioactive Cyclophosphazenes, and the Relationship to Inorganic Macromolecules," Proc. of Int. Symp. on Inorg. Ring Systems, Amherst, Mass., *Phosphorus, Sulfur and Silica*, 1989, 41, 119–133.

Allcock, H. R., "Polyphosphazenes as New Biomedical and Bioactive Materials," Chapter in *Biodegradable Polymers as Drug Delivery Systems*, (R. Langer and M. Chasin, eds), Marcel Dekker: New York 1990, 163–193.

Allcock, H. R., "Chemical Synthesis at the Boundary Between Polymer Chemistry and Inorganic Materials," *The Chemist*, 1990, 10–16.

Allcock, H. R., et al., "Ring–Opening Polymerization of Phosphazenes: Mechanism and Idiosyncrasies," *Polym. Prepr.* (Amer. Chem. Soc., Div. Polym. Chem.) 1990, 31, 48–50.

Allcock, H. R. and Chang, J. Y., "Poly(organophosphazenes) with Oligopeptides as Side Groups: Prospective Biomaterials," *Macromolcules* 1991, 24, 993–999.

Allcock, H. R. and Pucher, S. R., "Polyphosphazenes wtih Glucosyl and Methylamino, Trifluoroethoxy, Phenoxy, or (Methoxyethoxy)ethoxy Side Groups,38 *Macromolecules* 1991, 24, 23–34.

Allcock, H. R., et al., "Surface Reaction of Poly[bis(trifluoroethoxy)phosphazene] Films by Basic Hydrolysis," *Chemistry of Materials* 1991, 3, 442–449.

Allcock, H. R. and Fitzpatrick, R. J., "Functionalization of the Surface of Poly[bis(trifluoroethoxy)phosphazene] by Reactions with Alkoxide Nucleophiles," *Chemistry of Materials* 1991, 3, 450–454.

Allcock, H. R., et al., "Antibacterial Activity and Mutagenicity Studies of Water–Soluble Phosphazene High Polymers," *Biomaterials* 1992 13(12), 857–862.

Allcock, H. R., "Polyphosphazenes," Proc. of 1st U.S.–Japan Conference on Inorganic Polymers, Nagoya, Japan, 1991, *J. Inorg. and Organomet. Polymers* 1992, 2(2), 197–211.

Allcock, H. R., et al., "Oxidation of Poly[bis(4–methylphenoxy)–phosphazene] Surfaces and Chemistry of the Surface Carboxylic Acid Groups," *Chemistry of Materials* 1992, 4(4), 769–775.

Allcock, H. R., "Tailored Design of New Polyphosphazenes with Special Properties," Proceedings of Second Pacific Polymer Conference, Otsu, Japan, 1991 (Y. Iminishi, ed.) Springer–Verlag, 1992, pp. 89–100.

Allcock, H. R., "Rational Design and Synthesis of New Polymeric Materials", *Science* 1992, 255, 1106–1112.

Allcock, H. R., et al., "Thin–Layer Grafts of Poly[bis(methoxyethoxy)–ethoxy)phosphazene] on Organic Polymer Surfaces," *Chemistry of Materials* 1992, 4, 775–780.

Allcock, H. R., et al., "Polyphosphazenes Bearing Polymerizable Pyrrole, Thiophene, and Furan Side Groups: Synthesis and Chemical Oxidatiion," *Chemistry of Materials* 1992, 4, 780–788.

Allcock, H. R., et al., "Solid Polymeric Electrolytes Based on Crosslinked MEEP–Type Materials," *PMSE Prepr. (ACS Div. Polym. Mater., Science & Engin.)* 1993, 68, 76–77.

Bano, M. C., et al., "A Novel Synthetic Method for Hybridoma Cell Encapsulation," *Biotechnology* 1991, 9, 468–471.

Bennett, J. L., et al., "Radiation Crosslinking of Poly[bis(2–(2–methoxyethoxy)–ethoxy)phosphazene]: Effect on Solid State Ionic Conductivity," *Chemistry of Materials* 1989, 1, 14–16.

Bennett, J. L., et al., "Radiation Crosslinking of Poly[bis(2–(2–methoxyethoxy)–ethoxyphosphazene Effect on Solid State Ionic Conductivity," *Polym. Prepr. (ACS Polym. Div.)* 1989, 30(1), 437–438.

Blonsky, P. M., et al., "Polyphosphazene Solid Electrolytes," *J. Am. Chem. Soc.* 1984, 106, 6854–6855.

Cohen, S., et al., "An Ionically–Crosslinkable Polyphosphazene: A Novel Polymer for Microencapsulation," *J. Am. Chem. Soc.*, 1990, 112, 7832–7833.

Coley, S. M., et al., "The Polymerization Behavior of Pentachlorocyclo(carbotriphosphazene), $N_3P_2CCl_5$, *Polym. Prepr.* 1992, 33(2) 166–167.

Coqueret, X. et al., "Some Aspects of the Reactivity of Photo–Dimerizable Esters Grafted Onto Silicone Main Chain Polymers," *Makromol. Chem.* 1991, 1517–1535.

Davidson, R. S., and Lowe, C., "A Study of Some Photo– crosslinkable Resins Using i.r. Spectroscopy," *Eur. Polym. J.* 1989, 25(2) 167–172.

Davidson, R. S., and Lowe, C., "Use of u.v./Visible Photoacoustic Spectroscopy to Study the Photoinduced Crosslinking of Oligomers Containing Chalcone Units," *Eur. Polym. J.* 1989, 25(2), 159–165.

Gleria et al., "Photochemical Behavior of Poly(organophos–phazenes). 5. Photochemistry of Poly [bis(4–benzoylphenoxy)–phosphazene], [NP(OC6H$_4$COC$_6$H$_5$)$_2$]$_n$, in Solution," *Macromol.* 1987, 20, 1766–1770.

Gleria, M. et al., "Photochemical Behavior of Poly(Organophosphazenes). X. Photo–Cross–Linking Phenomena in Poly[Bis(4–Isopropylphenoxy)$_{0.8}$ (4–Benzoylphenoxy)$_{1.2}$ Phosphazene]," *J. Inorg. Organomet. Polym.* 1992, 2(3), 329–344.

Gleria, M. et al., "Photochemical Behaviour of Poly(Organophsophazenes)—Part VII. Direct and Sensitized Photochemistry of Poly[bis(4–isopropylphenoxy)]phosphazene in Solution and in Film," *Eur. Polym. J.* 1989, 25(10), 1039–1047.

Gleria, M. et al. "Photo–chemical Behaviour of Poly(Organophos–phazenes): Part VI—Photo– stabilization of Poly[bis(4–benzoylphenoxy)] phosphazene by Energy Transfer Processes," *Polym. Degrad. Stab.* 1988, 22, 125–135.

Hatanaka, H., et al., "Synthesis and Properties of Polymers Containing 4– or 4'–Chalconecarbonyl Groups in Side Chains," *M. Makromol. Chem.* 1975, 176, 3231–3242 (1975).

Kato, M., et al., "Novel Synthesis of Photocrosslinkable Polymers," *M. J. Poly. Sci. Pt. A–1* 1971, 9, 2109–2128.

Keller, P., "Photo–Cross–Linkable Liquid–Crystalline Side–Chain Polysiloxanes," *Chem. Mater.* 1990, 2, 3–4.

Kugel, R. L. et al., "The Formation of Radical Anions in Fluorene Metanation," *Chem. and Ind.* 1962, 1649–1650.

Laurencin C., et al., "Controlled Release Using a New Bioerodible Polyphosphazene Matrix System," *J. Biomed. Mater. Res.* 1987, 21, 1231–1246.

Laurencin, C. A., et al., "Use of Polyphosphazenes for Skeletal Tissue Regeneration," *J. Biomed. Mater Res.* 1993, 27, 963–973.

Malm, B., "Substituted and Branched Polychalcones: Syntheses and Characterization by Spectrometric Methods," *Makromol. Chem.* 1981, 182, 1307–1317.

Malm, B., and Lindberg, J. J., "Substituted and Branched Polychalcones, $2^a$): Polymeric and Solubility Properties of the Polychalcones," *Makromol. Chem.* 1981, 182, 2747–2755.

Manners, I., et al., "Poly(carbophosphazenes): A New Class of Inorganic–Organic Macromolecules," *J. Am. Chem. Soc.* 1989, 111, 5478–5480.

Mercier, R. et al., "Photochemistry of Polymeric Systems—VIII. Photo–Crosslinking of Polysiloxanes Including Cinnamic, Furacrylic or α–Cyano β–Styrylacrylic Ester Groups: A Comparative Study," *Eur. Polym. J.* 1988, 24(7), 639 . 645.

Minsk, L. M., et al., "Photosensitive Polymers. I. Cinnamate Esters of Poly(vinyl Alcohol) and Cellulose," *J. Appl. Polym. Sci.* 1959, 11, 302–307.

Neenan, T. X., and Allcock, H. R., "Synthesis of a Heparinized Poly(organophosphazene)," *Biomaterials* 1982, 3, 78–80.

Nelson, C. J., et al., "Ultraviolet Radiation–Induced Cross–linking of Poly [bis(2–(2–methoxy)ethoxy)phosphazene]," *Chemistry of Materials* 1991, 3, 786–787.

Nishikubo, T. et al., "Photosensitivity of Copolymers with Pendant Cinnamic Ester and Suitable Photosensitizer Groups," *Makrol. Chem. Rapid. Commun.* 1982, 3, 377–382.

O'Brien, J. P., et al., "The Photolysis of Poly(alkoxy– and aryloxyphosphazenes), [NP(OR)$_2$]$_n$,38 *Macromolecules* 1979, 12, 108–113.

Panda, S. P., "Photo–Crosslinkable Polymers with Benzylideneacetophenone (Chalkone) Structure in the Side Chains," *J. Appl. Polym. Sci.* 1974, 18, 2317–2326.

Panda, S. P., and Sadafule, P. S., "Photocrosslinkable Unsaturated Polyesters," *J. Appl. Polym. Sci.* 1979, 24, 511–521.

Panda, S. P., "New Photocrosslinkable Polymers with Chalcone Structure," *Indian J. Technol.* 1976, 14, 44–446.

Panda, S. P., "New Photocrosslinkable Polymer," *J. Armament Stud.* 1975, 11(1), 30–32.

Panda, S. P., "Synthesis & Characterization of Uncured Epoxy Resins Obtained from Condensation of Dihydroxychalcones with Epichlorohydrine: Part II—Explanation of the Doubling of vC=o in the Resins," *Indian J. Technol.* 1973, 11, 356–359.

Panda S. P., "Photocrosslinkable Resins with Benzylideneacetophenone (Chalcone) Structure in the Repeat Units," *J. Polym. Sci., Polym. Chem. Ed.* 1975, 13, 1757–1764.

Panda, S. P., "Synthesis & Characterization of Uncured Epoxy Resins Obtained by the Condensation of Dihydroxychalcones & Epichlorohydrin," *Indian J. Technol.* 1971, 9, 387–390.

Pucher, S. R. and Allcock, H. R., "Poly[(amino ester)phosphazenes]: Bioerodible Substrates for Controlled Drug Delivery," *Polym. Prepr.* 1982, 33(2), 108–109.

Ritchie, R. J., et al., "Polymerization of Monoalkylpentachlorocyclotriphosphazenes," *Macromolecules* 1979, 12(5), 1014–1015.

Rusu, G. I., et al., "Polychalkone. 5." *Makromol. Chem.* 1974, 175, 1651–1658.

Rusu, G. I., et al. "Polychalcones. 5. Electrical Properties of Heat–Resistant Polychalcones," *Chem. Abstr.* 1974, 82, 17595p.

Scopelianos, A. G. and Allcock, H. R., "Polymerization of Hexachlorocyclotri–phosphazenes in the Presence of Carbon Disulfide," *Macromolecules* 1987, 20, 432–433.

Unruh, C. C., "Polyvinyl–trans–benzalacetophenone)," *J. Appl. Polym. Sci.* 1959, 2(6), 358–362.

Unruh, C. C., "Poly(4'–vinyl–cis–benzalacetophenone)," *J. Polym. Sci.* 1960, 45, 325–340.

Visscher, K. B., et al., "Synthesis and Properties of Polyphosphazene Interpenetrating Polymer Networks" *Macromolecules* 1990, 23, 4885–4886.

Watanabe, S., et al., "Photochemicaly Active Modification of Polymers I. Preparation and Reaction of Photocrosslinkable Poly(vinyloxycarbonylchalcone)," *Polym. Sci. Pt. A. Polym. Chem.* 1986, 24, 1227–1237.

Watanabe, S., et al., "Preparation and Properties of Photocrosslinkable Poly(2–Vinyloxethyl Cinnamate)," *Polym Sci. Polym. Chem.* 1984, 22, 2801–2808.

Welker, M. F., et al., "The Effects of Radiation on Newly Synthesized Allylamino–Substituted Polyphosphazenes," *Polym. Prep.* 1992, 66, 259–260.

PHOTOCROSSLINKABLE POLYPHOSPHAZENES AND THEIR USE AS MICROENCAPSULATION MATERIALS

The United States Government may have certain rights in this invention by virtue of a grant from the Office of Naval Research.

This invention is in the area of polymer chemistry, and in particular in the area of photocrosslinkable chalcone bearing and cinnamate-bearing polyphosphazenes. These polymers are useful in photolithography, photocurable coatings, for the stabilization of certain non-linear optical properties, and for use in the construction of biocompatible semi-permeable membranes which can be used to encapsulate living cells or other substances of implantation.

BACKGROUND OF THE INVENTION

The field of photocrosslinkable polymers has been widely studied and is of broad current interest. These polymers are used in the preparation of photoresists for use in macro- and microlithography, chemically-resistant coatings, and in the field of non-liner optical (NLO) materials.

A classical photosensitive moiety is the cinnamate group, which has the formula $(C_6H_5)HC=C(H)CO_2-$. This moiety has been well-studied and widely used in photocrosslinkable polymers because its high sensitivity to UV radiation and the chemical resistance of the resultant polymers.

The cinnamate group crosslinks in a controlled 2+2 photo-induced cycloaddition. It is one crosslinking unit used in polymers for offset printing plates and microcomponents. Polymeric materials that incorporate the cinnamate group have existed since 1948. Minsk, L. M. et al, U.S. Pat. No. 2,690,966; Minsk, L. M., et al., *J. Appl. Polym. Sci.* 1959, 11, 302. The synthetic route to poly(vinyl cinnamate), in which poly(vinyl alcohol) is esterified with cinnamoyl chloride, serves as a model for the synthesis of a wide variety of photopolymers. Cinnamate containing photopolymers that have acrylate and other vinyl backbones have also been synthesized. Minsk, et al., U.S. Pat. No. 2,690,966; Minsk, L. M. et al., *J. Appl. Polym. Sci.* 1959, 11, 302; Nishikubo, T. et al., *Makrol. Chem. Rapid. Commun.* 1982, 3, 377; Mercier, R. et al., *Eur. Polym. J.* 1988, 24, 639; Keller, P. *Chem. Mater.* 1990, 2, 3; Coqueret, X. et al. *Makromol. Chem.* 1991, 1517.

Another photosensitive unit is the chalcone group, which has the formula $-(C_6H_4)-CH=CHC(O)-(C_6H_5)$. Chalcones are particularly useful in the preparation of photocrosslinkable polymers because of the high overall photosensitivity of the chalcone unit, which is a result of the close match between the absorption spectrum of the chalcone side group and the emission spectrum of a mercury arc UV light source. This close spectral match allows for high photocrosslinking efficiency without the use of an added sensitizer.

Polymeric materials that contain chalcone-type groups have existed since 1959. These species include macromolecules with chalcone-type groups in the side chain (see, for example, Unruh, C. C. *J. Appl. Polym. Sci.* 1959, 6, 358; Akelah, A., et al., *Polym. Int.* 1992, 28, 307; Unruh, C. C. *J. Polym. Sci. PtA-1* 1960, 45, 325; Watanabe, S., et al., *Polym. Sci. Pt. A. Polym. Chem.* 1986, 24, 1227; Watanabe, S., et al. , *Polym. Sci. Polym. Chem.* 1984, 22, 2801; Kato, M., et al., *M. J. Polym. Sci. Pt.* A-1 1971, 9, 2109; Panda, S. P. *J. Appl. Polym. Sci.* 1974, 18, 2317; Hatanaka, H., et al., *M. Makromol. Chem.* 1975, 176, 3231; Panda, S. P., Sadafule, P.S. *J. Appl. Polym. Sci.* 1979, 24, 511; Panda, S. P. *Indian J. Technol.* 1976, 14, 444; and Panda, S. P. *J. Armament Stud.* 1975, 11, 30), in the main chain, (see, for example, Malm, B. *Makromol. Chem.* 1981, 182, 1307; Panda, S. P. *Inst. Armament Technol.* 1973, 11, 356; Davidson, R. S., Lowe, C. *Eur. Polym. J.* 1989, 25, 159; Malm, B., Lindberg, J. J. *Makromol. Chem.* 1981, 182, 2747; Rusu, G. I., Oleinek, H., Zugravescu, I. *Makromol. Chem.* 1974, 175, 1651; and *Chem. Abstr.* 1974, 82, 17595p.) and in epoxy resins (See, for example, Panda, S. P., *J. Polym. Sci., Polym. Chem. Ed.* 1975, 13, 1757; Davidson, R. S., Lowe, C. *Eur. Polym. J.* 1989, 25, 167; Davison, R. S., Lowe, C. *Eur. Polym. J.* 1989, 25, 159; Panda, S. P. *Indian J. Technol.* 1971, 9, 387) Due to the solubility difficulties arising from the rigid-rod nature of main-chain-containing chalcone polymers, a recent emphasis has been on polymers with side chain chalcone units.

Polyphosphazenes are a class of polymers which have been reported to exhibit a number of interesting properties. The photochemical behavior and stability of poly(aryloxyphosphazenes) have been described previously. See, for example, Allcock, et al., *Macromol.*, 1979, 12, 108; and Gleria et al., *Macromol.*, 1987, 20, 1766. While the phosphazene backbone has been used in the field of UV-crosslinkable materials (see, for example, Gleria, M. et al., *J. Inorg. Organomet. Polym.* 1992, 2, 329; Gleria, M., *Eur. Polym. J.* 1989, 25, 1039; Gleria, M. et al. *Polym. Degrad. Stab.* 1988, 22, 125; Nelson, C. J.; Coggio, W. D.; Allcock, H. R. *Chem. Mater.* 1991, 3, 786; O'Brien, J. P.; Ferrar, W. T.; and Allcock, H. R. *Macromolecules* 1979, 12, 108), the use of a polyphosphazene backbone as a platform for photocrosslinkable cinnamate side groups has not been reported.

The phosphazene skeletal system has several advantages that could be exploited for photopolymer applications. These include: (1) the number of potential cross-linkable groups per repeat unit; (2) the ability to incorporate a wide variety of cosubstituents via macromolecular substitution in polyphosphazenes, which allows properties such as the glass transition temperature, solubility, lipophilicity, and biocompatibility to be tailored at will; and (3) the absence of an absorption of the polyphosphazene backbone in the mid-UV to the near infrared region, which minimizes photoinduced reactions of the skeletal system during the UV irradiation required for the photocrosslinking procedure.

Examples of known poly(organophosphazenes), and methods for their synthesis include those described in U.S. Pat. No. 4,278,660 (which discloses that square planar platinum complexes that are useful as chemotherapeutic agents can be rendered less toxic by administration in combination with a polyphosphazene), U.S. Pat. No. 4,440,921 (which discloses that biologically active molecules containing a carboxylic acid residue can be covalently attached to a polyphosphazene via condensation with a pendant amino group on the polyphosphazene), U.S. Pat. No. 4,451,647 (which teaches that heparin can be attached to an organophosphazene polymer without disrupting the polymer backbone via complexation with a quaternary ammonium ion covalently attached to the polyphosphazene backbone), U.S. Pat. No. 4,880,622 (which discloses novel poly(organophosphazene) polymers that are useful for the controlled delivery of pharmaceuticals, pesticides, herbicides, plant growth regulators, and fertilizers), U.S. Pat. No. 5,053,451 (which discloses that poly(carboxylatophenoxy)phosphazene can be ionically crosslinked to form a hydrogel), and U.S. Pat. No. 5,149,543 (which discloses a composition that includes a biological material such as a liposome, virus, procaryotic cell, or eucaryotic cell encapsulated in an ionically crosslinked polyphosphazene or other polyelectrolyte).

In light of the established utility of cinnamates and chalcones as photosensitive units, as well as the diverse properties of polyphosphazenes, it would be of interest for a variety of applications to provide cinnamate and chalcone-bearing phosphazenes, and in particular, polymeric phosphazenes.

It is therefore an object of the present invention to provide both small molecule model cyclic trimers and high polymeric phosphazenes that bear chalcone or cinnamate containing pendant groups.

SUMMARY OF THE INVENTION

Chalcone and cinnamate bearing polyphosphazenes are disclosed. The polyphosphazenes contain a sufficient number of chalcone or cinnamate groups, or a combination thereof, to achieve a photocrosslinkable material. The phosphazene backbone is transparent from the near and mid-UV to the near infrared region, minimizing degradation of the skeleton both under the high intensity UV irradiation required for the photo-crosslinking reaction and during subsequent exposure to light. disclosed.

These photosensitive polyphosphazenes are useful for a variety of purposes, including in photolithography, photocurable coatings, for the stabilization of certain non-linear optical properties, and for use in the construction of biocompatible semi-permeable membranes which can be used to encapsulate living cells or other substances of implantation.

DETAILED DESCRIPTION OF THE INVENTION

Figure 1:
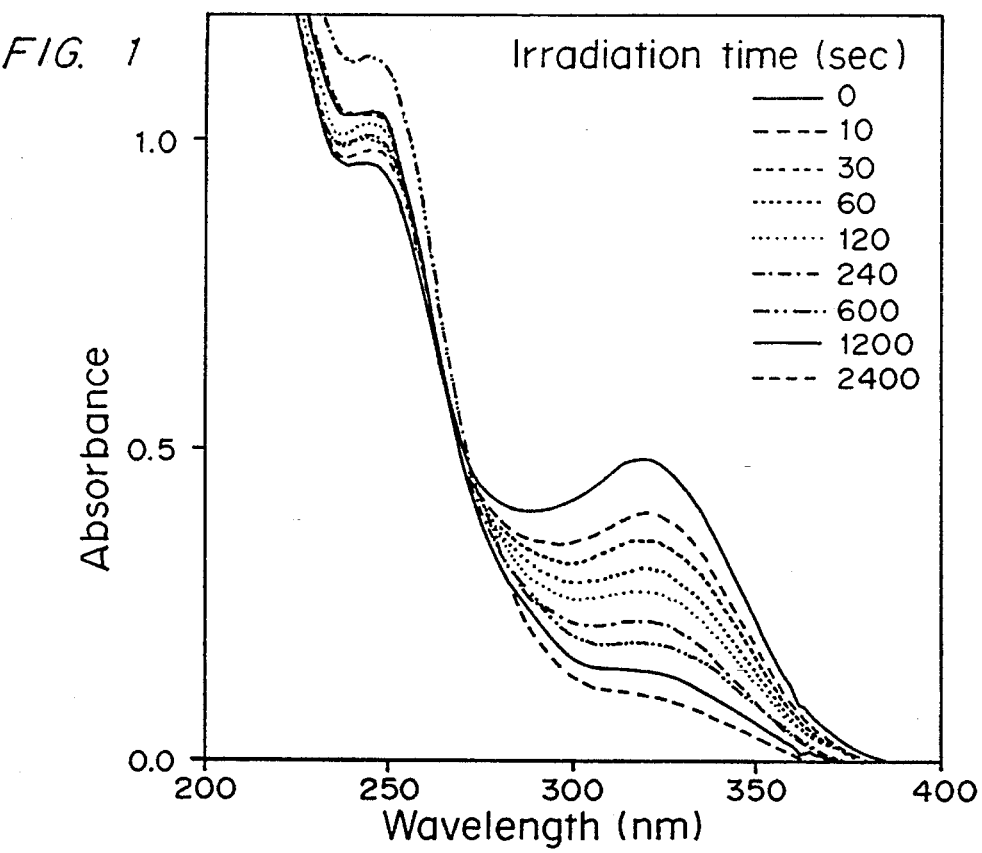
FIG. 1 is a graph of the effect of UV irradiation in time (seconds) on the UV absorption of $[NP\{OC_6H_4CH=CHC(O)C_6H_5\}_2]_n$, referred to as polymer 6.

Chalcone and cinnamate bearing polyphosphazenes are disclosed. The polyphosphazenes contain a sufficient number of chalcone or cinnamate groups, or a combination thereof, to achieve a photocrosslinkable material. The phosphazene backbone is transparent from the near and mid-UV to the near infrared region, minimizing degradation of the skeleton both under the high intensity UV irradiation required for the photo-crosslinking reaction and during subsequent exposure to light.

The photosensitive polyphosphazene can also contain any number of other substituent groups to tailor the physical properties of the polymer to a selected specific application. When two photocrosslinkable groups are present per repeat unit in the polyphosphazene, a high cross-link density following UV irradiation is accomplished.

These photosensitive polyphosphazenes are useful for a variety of purposes, including in photolithography, photocurable coatings, for the stabilization of certain non-linear optical properties, and for use in the construction of biocompatible semi-permeable membranes which can be used, for example, to encapsulate living cells or other substances for implantation.

The photosensitive polyphosphazenes can also be used for the preparation of gas-filled polymeric microbubbles, which are useful in the process of diagnostic ultrasound imaging, and can be prepared in micron and submicron sizes that are injectable and that are capable of passing through the pulmonary capillary bed.

Phosphazene cyclic trimers that bear one or more of the substituent groups of interest can be used as models for the photocrosslinking of the related high polymers. Photoreactivity studies with small molecules are facilitated by the ease of solution characterization using $^1H$, $^{13}C$ and $^{31}P$ NMR spectroscopy, UV spectroscopy and mass spectrometry.

I. Definitions

A. General Definitions

The term alkyl, as used herein, refers to a saturated straight, branched, or cyclic (in the case of $C_3$ or greater) hydrocarbon, or a combination thereof, typically of $C_1$ to $C_{20}$, and specifically includes methyl, ethyl, propyl, isopropyl, cyclopropyl, cyclobutyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, decyl, or dodecyl.

The term lower alkyl, as used herein, refers to a saturated straight or branched hydrocarbon or a combination thereof, typically of $C_1$ to $C_6$, or a cyclic hydrocarbon of $C_3$ or greater, and specifically includes methyl, ethyl, propyl, isopropyl, cyclopropyl, butyl, cyclobutyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl or aromatic, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(alkyl), —$CO_2H$, —$OSO_2H$, —$SO_3H$, —$PO_3H$, —$CO_2$alkyl, amide, amino, alkylamino and dialkylamino, and wherein the aryl group can have up to 3 substituents.

The term aliphatic refers to a hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent, including p-methylphenyl.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term heteroalkyl, as used herein, refers to an alkyl group that includes a heteroatom such as oxygen, sulfur, or nitrogen (with valence completed by hydrogen or oxygen) in the carbon chain or terminating the carbon chain. Examples of these compounds include a series of lower alkyls interrupted by a heteroatom such as oxygen, sulfur or nitrogen, including —O—[(alkyl)O]$_x$—CH$_2$)$_y$NH$_2$, wherein the alkyl group can vary within the moiety, including —O—[(CH$_2$)$_x$O]$_y$—CH$_2$)$_x$NH$_2$; —O—[(CH$_2$)$_x$O]$_y$CH$_2$)$_x$NH(CH$_2$)$_x$SO$_3$H, and —O—[(alkyl)—O]y— (alkyl), wherein the alkyl group can vary within the moiety, including —O—[(CH$_2$)$_x$O]$_y$—(alkyl), wherein x is 1–8 (which can vary within the moiety) and y is an integer of 1 to 40. Specific examples of these compounds include methoxyethoxyethoxy, ethoxyethyoxy and methoxyethoxy.

The term poly(organophosphazene), as used herein, refers to a polyphosphazene in which one or more of the pendant groups contain carbon.

The term biologically active molecule or material as used herein refers to an organic molecule including a drug, a protein, polysaccharide, nucleoprotein, lipoprotein, synthetic polypeptide, or a small molecule linked to a protein, carbohydrate, glycoprotein, steroid, nucleic acid, nucleotide, nucleoside, oligonucleotides (including antisense oligonucleotides), cDNA, nucleic acids, genes, vitamins, including vitamin C and vitamin E, lipid, cell or cell line or combination thereof, that causes a biological effect when administered in vivo to an animal, including but not limited to birds and mammals, including humans. The term drug, as used herein, refers to any substance used internally or externally as a medicine for the treatment, cure, or prevention of a disease or disorder, and includes but is not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds.

The term biodegradable polymer refers to a polymer that degrades within a period that is acceptable in the desired application, less than several week or months and typically less than a year, when exposed to a physiological solution of pH between 6 and 8 having a temperature of between about 25° C. and 37° C.

The term amine, as used herein, refers to an amino group having one or two substituents selected from: alkyl, alkenyl, alkynyl, aryl, aralkyl, alkaryl, heteroaryl and heteroalkyl that are optionally substituted with one or more substituents as defined for the aryl groups above, and specifically includes halo and hydroxy. These substituents may be further substituted with groups, including halo and hydroxy. Non-limiting specific examples of suitable amines include tetraethylenepentaamine and triethylenetetraamine.

B. Poly (organophosphazenes)

Poly(organophosphazenes) are polymers of general formula (I):

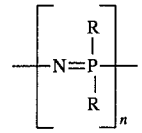

wherein n is an integer.

Poly(organophosphazenes) of Formula I are easily synthesized from poly(dichlorophosphazene) by replacement of the highly reactive chlorine atoms with the desired organic side chains. The properties of the resulting poly(organophosphazenes) can be controlled by the appropriate selection of the R groups.

A sufficient number of the R groups must be either a chalcone, a cinnamate, or other unsaturated moiety that will crosslink under appropriate conditions. Derivatives of chalcones or cinnamate groups, for example that bear additional alkyl or aryl groups in place of hydrogen, or wherein the phenyl groups are optionally substituted, can be used in place of the chalcone or cinnamate.

The cinnamate moiety can be bonded to the polyphosphazene through the carboxyl group, or alternatively, through a nucleophilic substituent such as hydroxyl or amino on the aryl group. Likewise, the chalcone can be bonded to the polyphosphazene through a nucleophilic substituent on either of the aryl groups. One or more non-chalcone/cinnamate substituents be included in the polymer as desired.

Poly(organophosphazenes) can be formed with two or more types of pendant groups by reacting poly(dichlorophosphazene) with two or more nucleophiles in a desired ratio. In general, when the poly(organophosphazene) has more than one type of pendant group, the groups will vary randomly throughout the polymer. Thus, the poly(organophosphazene) will contain phosphorous atoms which are bound to two like groups or two different groups. The resulting ratio of the two or more pendant groups in the poly(organophosphazene) will be determined by a number of factors, including the ratio of starting materials used to produce the polymer, the reactivity of the nucleophile, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

The properties of the poly(organophosphazenes) such as its degree of hardness, Tg, hydrophilicity, hydrogel or organogel character, acidity, and film forming ability can be controlled through proper selection of the R groups.

Non-limiting examples of non-chalcone/cinnamate R groups include but are not limited to aliphatic, aryl, aralkyl, alkaryl, amino acid, amino acid ester, carboxylic acid, heteroaromatic, carbohydrate, including glucose, heteroalkyl, halogen, (aliphatic)amino- including alkylamino-, heteroaralkyl, di(aliphatic)amino- including dialkylamino-, arylamino-, diarylamino-, and alkylarylamino-, -oxyaryl including but not limited to -oxyphenyl-p-methyl, -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic)PO$_3$H, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, and -thioaralkyl, organosilicon, including but not limited to -(alkyl)—Si(alkyl)$_4$, including —CH$_2$Si(CH$_3$)$_4$; —NH-C(O)O—(aryl or aliphatic), —O—([(alkyl)O]$_x$—CH$_2$)$_y$NH$_2$, wherein the alkyl group can vary within the moiety, including —O—[(CH$_2$)$_x$O]$_y$—CH$_2$)$_x$NH$_2$; —O—[(CH$_2$)$_x$O]$_y$CH$_2$)$_x$NH(CH$_2$)$_x$SO$_3$H, and —O—[(alkyl)—O]$_y$—(aryl or aliphatic), wherein the alkyl group can vary within the moiety, including —O—[(CH$_2$)$_x$O]$_y$—(aryl or aliphatic), wherein x is 1–8 (which can vary within the moiety) and y is an integer of 1 to 40. The groups can be bonded to the phosphorous atom through, for example, a nucleophilic oxygen, sulfur, nitrogen, or carbon atom. In a preferred embodiment, n is greater than 4, for example, between 10 and 30,000, and more usually between 1000 and 20,000.

The following non-limiting examples are intended to illustrate the preparation of the polyorganophosphazenes of the present invention. Those skilled in the art will appreciate that modifications can be made to these examples, which are intended to fall within the scope of the present invention.

II. Preparation of Polyphosphazenes

Polyphosphazene polymers can be prepared by the reaction of an organic nucleophile with poly(dichlorophosphazene). See, for example, Allcock, H. R.; Austin, P. E.; Neenan, T. X.; Sisko, J. T.; Blonsky, P. M.; Shriver, D. F. *Macromol.*, 1986, 19, 1508, and Blonsky, P. M.; Shriver, D. F.; Austin, P. E.; Allcock, H. R. *J. Am. Chem. Soc.* 1984, 106, 6854.

Detailed procedures for the preparation of cinnamate and chalcone bearing polyphosphazenes are provided in Examples 1 to 38. Unless otherwise specified, the reactions were performed under an atmosphere of dry argon using standard Schlenk line techniques. Column chromatography was carried out with the use of silica as a stationary phase with the eluents as indicated in the specific example. Hexachlorocyclotriphosphazene (Ethyl Corporation) was recrystallized from hexane and sublimed (40° C., 0.05 nm Hg) before use. Tetrahydrofuran (THF) and dioxane were distilled from sodium benzophenone under dry argon before use. Triethylamine was distilled from calcium hydride in an atmosphere of argon before use. 2,2,-Trifluoroethanol (Halocarbon) was distilled from anhydrous barium oxide and was stored over 4 Å molecular sieves. 4-Hydroxychalcone was obtained from Lancaster Synthesis (Windham, N.H.) and was used as received. Phenol (Aldrich) was dried azeotropically with benzene before use and was stored under argon. All other reagents and solvents were used as received. Poly(dichlorophosphazene) was prepared by the standard literature procedures, see, for example, Allcock, H. R., Kugel, R. L. *J. Am. Chem. Soc.* 1965, 87, 4216; Allcock, H. R., Kugel, R. L., Valan, K. J. *Inorg. Chem.* 1966, 5, 1709; and Allcock, H. R., Kugel, R. L. *Inorg. Chem.* 1966, 5, 1716.

The analyses were performed using the techniques and instruments set forth below. High field $^{31}$P (146 MHz), $^{13}$C (90 MHz) and $^1$H (360 MHz) NMR spectra were obtained from a Bruker WM360 spectrometer. $^{13}$C (50 MHz) and $^1$H (200 MHz) NMR spectra were also obtained from a Bruker WP200 spectrometer or a Bruker ACE200 spectrometer. Nuclear Overhauser Effect (NOE) difference spectra were obtained from a Bruker AM300 spectrometer. Both $^{13}$C and $^{31}$P NMR spectra were proton decoupled unless otherwise specified. $^{31}$P NMR spectra were referenced to external 85% H$_3$PO$_4$ with positive shifts recorded downfield of the reference. $^1$H and $^{13}$C NMR spectra were referenced to external tetramethylsilane.

Elemental analyses were by Galbraith Laboratories Knoxville, Tenn.

Irradiations were accomplished with the use of a "Blak-Ray" ultraviolet lamp (Ultra-Violet Products, Inc., San Gabriel, Calif.) or a Canrad-Hanovia medium-pressure, quartz, mercury vapor lamp equipped with a water-cooled quartz immersion well.

Electron-impact mass spectra (EI/MS) were obtained from Kratos MS 9/50 equipment. Chemical ionization (CI) mass spectra were obtained from a Kratos MS-25 spectrometer. Fast Atom Bombardment (FAB) mass spectra were obtained with use of a Kratos MS-50 spectrometer.

Molecular weights were determined with a Hewlett-Packard HP1090 gel permeation chromatograph equipped with a HP-1037A refractive index detector and a Polymer Laboratories PL gel 10-μm column. The samples were eluted with a 0.1% by weight solution of tetra-n-butyl ammonium bromide in THF. The GPC column was calibrated with polystyrene standards (Waters) and with fractionated samples of poly[bis(trifluoroethoxy)phosphazene] provided by Drs. R. Singler and G. Hagnauer of the U.S. Army Materials Research Laboratories, Watertown, Mass.

UV-Visible spectra of all compounds as solutions in spectroscopic grade THF or methanol were obtained by means of a Hewlett-Packard Model HP8450A UV-Visible spectrometer. The spectra were recorded in quartz cells (1-cm path length) or on quartz plates for solid polymeric samples.

Glass transition temperatures were determined by differential scanning calorimetry (DSC) using a Perkin-Elmer-7 thermal analysis system equipped with a Perkin-Elmer 7500 computer. Heating rates of 10°–40° C./min under a nitrogen atmosphere were used. Sample sizes were between 10 and 30 mg.

A. Preparation Of Chalcone-Bearing Cyclic Trimeric Phosphazenes

One process for the preparation of cyclic trimeric phosphazenes used as reaction models for the high polymers is shown in Scheme 1.

Scheme 1

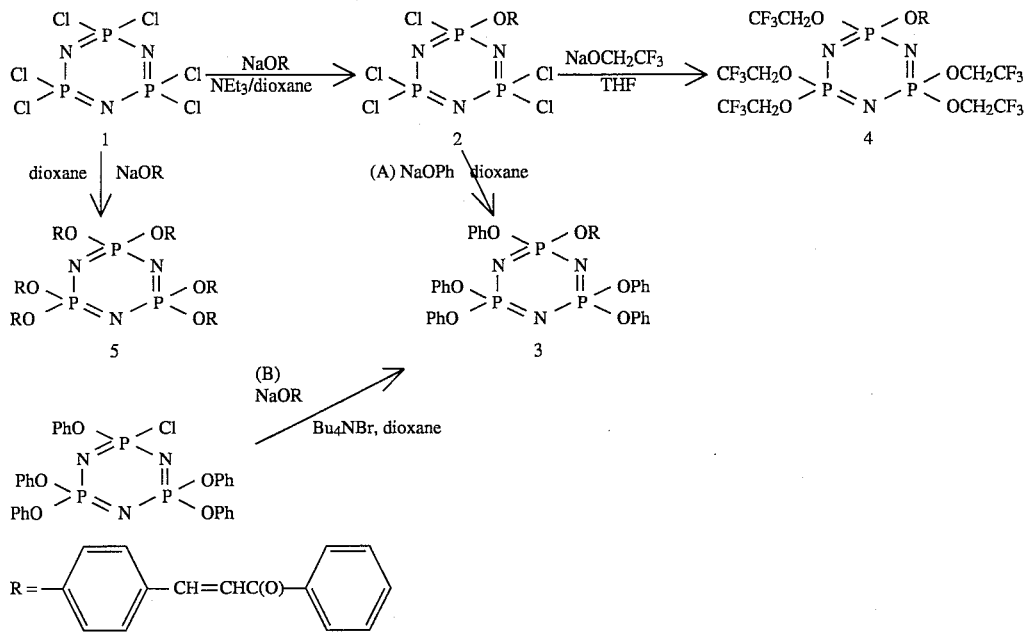

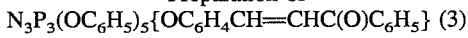

Scheme 1: Preparation of cyclic trimeric phosphazenes

The primary model system was simplified by use of monofunctional cyclotriphosphazenes. In addition, a hexachalcone-substituted cyclic trimer was prepared to model a polymer in which every phosphorous atom bear two photosensitive side groups.

EXAMPLE 1

Preparation of
$N_3P_3Cl_5\{OC_6H_4CH\!=\!CHC(O)C_6H_5\}$ (2)

4-Hydroxychalcone (2.58 g, 11.52 mmol) was added to a solution of hexachlorocyclotriphosphazene 1 (4.0 g, 11.50 mmol) in dioxane (250 mL) and triethylamine (15 mL). The solution was heated at reflux overnight and filtered. The solvent was removed under reduced pressure and the oil was chromatographed on silica using THF/hexane as the eluents. Trimer 2 was obtained in 35% yield. $^{31}P$ NMR (146 MHz, CDCl$_3$) AM$_2$ V$_A$=12.7 ppm, v$_B$=23.1 ppm, $^JPNP$=61 Hz; $^1H$ NMR (200 MHz, CDCl$_3$) δ 8.06–8.00 (d, 2 H), 7.84–7.47 (m, 7 H), 7.37–7.31 (m, 2 H); $^{13}C$ NMR (90 MHz, CDCl$_3$)δ 190.2, 150.7 (d, J=10.4 Hz), 143.0, 138.1, 133.7 (d, J=2.2 Hz), 133.0, 130.05, 128.8, 128.6, 123.0, 122.0 (d, J=5.5 Hz). MS, m/z calcd 535, m/z found 536 (MH$^+$). $\lambda_{max}$ (THF)=315 nm. mp, 112°–115° C.; Anal. Calcd for $C_{15}H_{11}Cl_5N_3O_2P_3$: C, 33.65; H, 2.07; N, 7.85; P, 17.35; Cl, 33.10. Found: C, 33.49; H, 2.19; N, 8.10; P, 17.89; Cl, 32.70.

EXAMPLE 2

Preparation of
$N_3P_3(OC_6H_5)_5\{OC_6H_4CH\!=\!CHC(O)C_6H_5\}$ (3)

Trimer 3 was synthesized via two routes. Route A involved the addition of 5.2 equivalents of sodium phenoxide to trimer 2 at 12° C., followed by warming to 45° C. for twelve hours. Route B involved the treatment of $N_3P_3(OPH)_5Cl$ with three equivalents of $NaOC_6H_4CH\!=\!CHC(O)C_6H_5$ in the presence of Bu$_4$NBr in dioxane heated to reflux. Both routes gave nearly quantitative yields of trimer 3. However, route A is preferred due to the shorter reaction time and less drastic reaction conditions required. Route A is set forth in detail below.

Sodium phenoxide was prepared from phenol (1.05 g, 11.2 mmol) and sodium metal (0.26 g, 10.8 mmol) in dioxane (250 mL). To the sodium salt solution at 10° C. was added 2 (1.0 g 2.87 mmol) in dioxane (40 mL) over one hour with stirring. The solution was allowed to warm slowly to room temperature and was stirred overnight at 40° C. The solvent was removed under reduced pressure and the residue was chromatographed on silica using THF/hexane as the eluents to obtain a pale yellow oil. $^{31}P$ NMR (146 MHz CDCl$_3$) δ 9.36–9.11 (m); $^1H$ NMR δ 8.06–8.01 (m, 2 H), 7.81–7.73 (d, 2 H, J=16 Hz), 7.62–7.40 (m, 5 H), 7.3–6.91 (m, 28 H). MS, m/z calcd 823, m/z found 824 (+FAB). UV: $\lambda_{max}$ (THF)=315 nm. Anal. Calcd for $C_{45}H_{36}N_3O_7P_3$: C, 65.62; H, 4.41; N, 5.10; P, 11.28. Found, C, 65.43; H, 4.51; N, 5.18; P, 11.40.

EXAMPLE 3

Preparation of
$N_3P_3\{OCH_2CF_3\}_5\{OCH\!=\!CHC(O)C_6H_5\}$ (4)

2,2,2-Trifluoroethanol (0.97 g, 9.7 mmol) was added to a suspension of sodium metal (0.22 g, 9.17 mmol) in THF (50 mL). This solution was stirred overnight and was then added over two hours to a solution of 2 (1.0 g, 1.86 mmol) in THF (50 mL) cooled to −80° C. The mixture was stirred for one hour after the addition of NaOCH$_2$CF$_3$ was complete and was then allowed to warm slowly to room temperature. After the mixture had been stirred overnight at room temperature, the solvent was removed by rotary evaporation and the residue was dissolved in diethyl ether (200 mL) and washed with water (3×100 mL). The organic layer was dried (MgSO$_4$), the solvent removed, and the oil was dissolved in 8 mL 40% THF/hexane. The oil was chromatographed on silica using increasing amounts of THF in hexane (0→50%, 5% increments, 500 mL fractions) to yield a pale yellow oil. MS, m/z calcd 853, m/z found 853.5 (+FAB). $_1$H NMR (CDCl$_3$, 200 MHz) δ 8.06–8.00 (m, 2 H), 7.76 (d, 1 H, J=15 Hz), 7.67–7.43 (m, 6 H), 7.37–7.23 (m, 2 H), 4.49–4.37 (m, 2 H (OCH$_2$CF$_3$ gem to OAr) ) 4.35–4.18 (m, 4 H, OCH$_2$CF$_3$ trans to OAr)) 4.08–3.80 (m, 4 H (OCH$_2$CF$_3$ cis to OAr)); $^{31}$P NMR (CDCl$_3$ 146 MHz): AM$_2$ v$_A$=17.4 ppm, v$_B$.13.7 ppm, ($^J$PNP=92 Hz). UV (THF): λ$_{max}$=308 nm. Anal. Calcd for C$_{25}$H$_{21}$F$_{15}$N$_3$O$_7$P$_3$: C, 35.19; H, 2.48; N, 4.92; P, 10.89; F, 33.39. Found: C, 34.96; H, 2.48; N, 4.93; P, 10.03%; F, 32.01.

The structure of trimer 4 was further elucidated by Nuclear Overhauser Effect (NOE) difference spectroscopy. In the $^1$H NMR spectrum, the trifluoroethoxy group geminal to the aryloxy group, and the four other trifluoroethoxy groups non-geminal to the aryloxy group, were found to be non-equivalent. However, non-equivalency was detected in the four non-geminally substituted trifluoroethoxy groups. A slight NOE effect was detected in the aryloxy protons when the signal at 3.97 ppm was irradiated, thus allowing the assignment of this signal as that of those trifluoroethoxy groups cis to the aryloxy group.

EXAMPLE 4

Preparation of [NP{OC$_6$H$_4$CH=CHC(O)C$_6$H$_5$}$_2$]$_3$ (5)

4-Hydroxychalcone (5.79 g, 25.8 mmol) was added to a suspension of NaH (0.62 g, 26.0 mmol) in dioxane (250 mL). The orange-colored solution was heated gently overnight, after which solid 1 (1.0 g, 2.87 mmol) was added. The solution was then heated at reflux for four days. The solvent was removed by rotary evaporation and the yellow oil was chromatographed on silica using THF/hexane as the eluent. Yield: 1.29 g (30%). $^1$H NMR (CDCl$_3$, 200 MHz) δ 8.00–7.94 (m, 2 H), 7.77 (d, 1 H, J=16 Hz), 7.61–7.41 (m, 6 H), 7.06 (d, 2 H, J=9 Hz); $^{13}$C NMR (CDCl$_3$, 90 MHz) δ 189.9, 151.9, 143.1, 137.9, 132.9, 132.2, 129.7, 128.6, 128.4, 122.1, 121.4. Anal. Calcd for C$_{90}$H$_{66}$N$_3$O$_{12}$P$_3$; C, 73.31: H, 4.51; N, 2.85. Found: C, 72.59; H, 4.45; N, 2.70; MS, m/z calcd 1473, m/z found 1475 (MH$^+$) (+FAB).λ$_{max}$ (THF): 312 nm.

B. Preparation of Chalcone-bearing Polyphosphazene Polymers

One example of a synthetic pathway for the preparation of polymers 6, 7 and 8 is illustrated in Scheme 2.

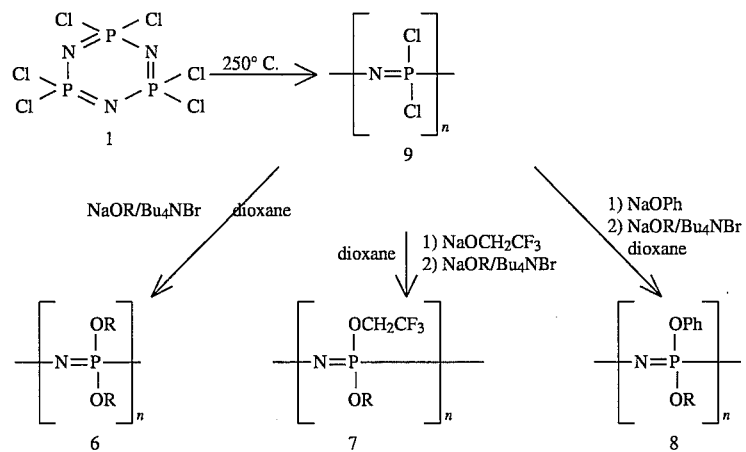

Scheme 2: Preparation of Polyorganophosphazene Polymers bearing Chalcone Substituents Poly(dichlorophosphazene) 9 was prepared by the thermal ring opening polymerization of 1.

EXAMPLE 5

Preparation of [NP{OC$_6$H$_4$CH=CHC(O)C$_6$H$_5$}$_2$]$_n$ (6)

4-Hydroxychalcone (7.72 g, 34.75 mmol) was added to a suspension of NaH (0.83 g, 34 mmol) and Bu$_4$ NBr in dioxane (250 mL). After this solution had been heated at 35° C. overnight, it was added dropwise to a solution of poly-(dichlorophosphazene) 9 (1.0 g, 8.6 mmol) in dioxane (500 mL). The solution was heated for 11 days at reflux. The solvent was removed under reduced pressure and the polymeric product was isolated and purified by precipitation of viscous THF solutions into water (4 times), isopropanol (2 times) and hexane (1 time). $^1$H NMR (CDCl$_3$, 200 MHz) δ 7.70–6.68 br, m; $^{13}$C NMR (CDCl$_3$, 50 MHz) δ 189.41, 152.36, 142.65, 137.59, 132.70, 131.39, 129.53, 128.47, 128.39, 121.43, 120.99; $^{31}$P NMR (CDCl$_3$, 146 MHz)δ-20.36. (s). λ$_{max}$=317 nm. (THF). M$_w$; 4.4×10$^6$; M$_n$: 6.1×10$^6$; M$_w$/M$_n$; 1.4. Anal. Calcd for C$_{30}$H$_{22}$O$_2$NP; C, 80.35; H, 4.91; N, 3.12; P, 6.75; Cl. O. Found: C, 71.87; H, 4.88; N, 2.54; P, 6.16; Cl, 0.026. T$_g$: 62° C.

EXAMPLE 6

Preparation of [NP{OCH$_2$CF$_3$}$_{0.93}${OC$_6$H$_4$CH=CHC(O)C$_6$H$_5$}$_{1.07}$]$_n$ (7)

A suspension of sodium metal (0.40 g, 16.7 mmol) in dioxane (150 mL) and 2,2,2—trifluoroethanol (1.73 g, 17.3 mmol) was stirred overnight. This suspension was added dropwise to a solution of 9 (2.0 g, 17.2 mmol) in dioxane (100 mL). After this solution had been stirred overnight at 35° C., a solution of NaOC$_6$H$_4$CH=CHC(O)C$_6$H$_5$ (prepared from HOC$_6$H$_4$CH=CHC(O)C$_6$H$_5$ (11.59 g, 51.7 mmol) and NaH (1.24 g, 52 mmol) and Bu$_4$NBr (0.55 g, 1.72 mmol) in dioxane (250 mL)) was added, and the resulting orange solution was heated to reflux for 10 days. The solvent was removed under reduced pressure to give a viscous solution which was poured slowly into water (4 times), isopropanol (1 time) and hexane (1 time) to precipitate the polymeric product. Anal. Calcd: C: 53.88; H, 3.45; N, 3.91; Cl, 0; F, 17.02. Found: C, 56.73; H, 3.98; N, 3.54; Cl, 0.52; f, 14.01. $^1$H NMR (CDCl$_3$, 360 MHz) δ 8.0–6.6 (Ar) (br), 4.1–3.7 (br) (OCH$_2$CF$_3$); $^{31}$P NMR (CDCl$_3$, 146 MHz) δ-9.75,-13.62, -17.89 (1:3:1); $^{13}$C NMR (CDCl$_3$, 90 MHz)δ 189.8, 140.0 (q, J=443 Hz), 132.9, 129.7, 128.7, 128.5, 127.8, 124.1, 121.9, 120.9, 62.9, M$_w$: 5.8×10$^6$; M$_n$: 4.4×10$^6$; M$_z$/M$_n$: 1.3. Tg; 44° C.

EXAMPLE 7

Preparation of [NP{OC$_6$H$_5$}$_1${OC$_6$H$_4$CH=CHC(O)C$_6$H$_5$}$_1$]$_n$ (8)

Phenol (2.43 g, 25.8 mmol) was added to a stirred suspension of NaH (0.62 g, 25.8 mmol) in dioxane (250 mL). After the solution had been stirred overnight at room temperature, it was added dropwise to 9 (3.0 g, 25.8 mmol) in dioxane (1000 mL). This solution was heated to 45° C. overnight. NaOC$_6$H$_4$CH=CHC(O)C$_6$H$_5$ (prepared from 17.3 g, 77.2 mmol HOC$_6$H$_4$CH=CHC(O)C$_6$H$_5$ in 300 mL dioxane) and Bu$_4$NBr (0.83 g, 2.6 mmol) were added over stirred at a gentle reflux for 9 days. The polymeric product was isolated by precipitations into water (4 times), isopropanol (2 times) and hexane (1 time). Anal. Calcd: C, 69.8; H, 4.4; N, 3.5; Cl, O. Found: C, 68.05; H, 4.66; N, 3.71; Cl, 0.68. $^1$H NMR (CDCl$_3$, 360 MHz) δ 7.8–6.8, br; $^{13}$C NMR (CDCl$_3$, 50 MHz) δ 189.70, 152.82, 151.06, 143.39, 137.87, 132.67, 130.75, 129.33, 129.10, 128.44, 128.34, 124.24, 121.17, 120.70; $^{31}$P NMR (CDCl$_3$, 146 MHz) δ - 19.2. M$_w$: 3.1×10$^6$; M$_n$ : 1.5×10$^6$; M$_w$/M$_n$: 2.1. T$_g$: 37° C.

The thermal behavior of polymers 6–8 was investigated with the aid of differential scanning calorimetry (DSC). The thermal analysis of chalcone-substituted polymers 6–8 indicated that all possessed T$_g$'s above room temperature, with polymer 6 having the highest T$_g$ at 62° C., which indicates a moderate degree of backbone stiffness induced by the sterically demanding side groups. The incorporation of the less hindered trifluoroethoxy and phenoxy cosubstituents lower the T$_g$'s of polymers 7 and 8, respectively to 44° and 37° C. The T$_g$'s of polymers 6–8 provide an excellent starting point for microlithographic, non-linear optical or surface coating applications.

EXAMPLE 8

Irradiation of Polymers 6, 7 and 8

The 2+2 cycloaddition reactions of polymers 6–8 were also investigated. Thin films of the polymers were cast onto a quartz plate from inhibition-free THF followed by complete removal of the casting solvent in vacuo. The λmax due to the chalcone chromophore was found to be 320 nm and was independent of the cosubstituent. This suggests minimal electronic interaction between side groups through the phosphazene backbone.

Solutions of polymers 6, 7 and 8 (approx. 0.1% w/v) were cast onto quartz plates. Following evaporation in air and vacuum drying, they were irradiated 23 cm from a "Blak-Ray" lamp equipped with a 260–380 nm band-pass filter for varying lengths of time. Sensitization experiments were accomplished with the above lamp in the absence of a filter on similar films with 1 weight percent of photosensitizer based on polymer.

Figure 2:
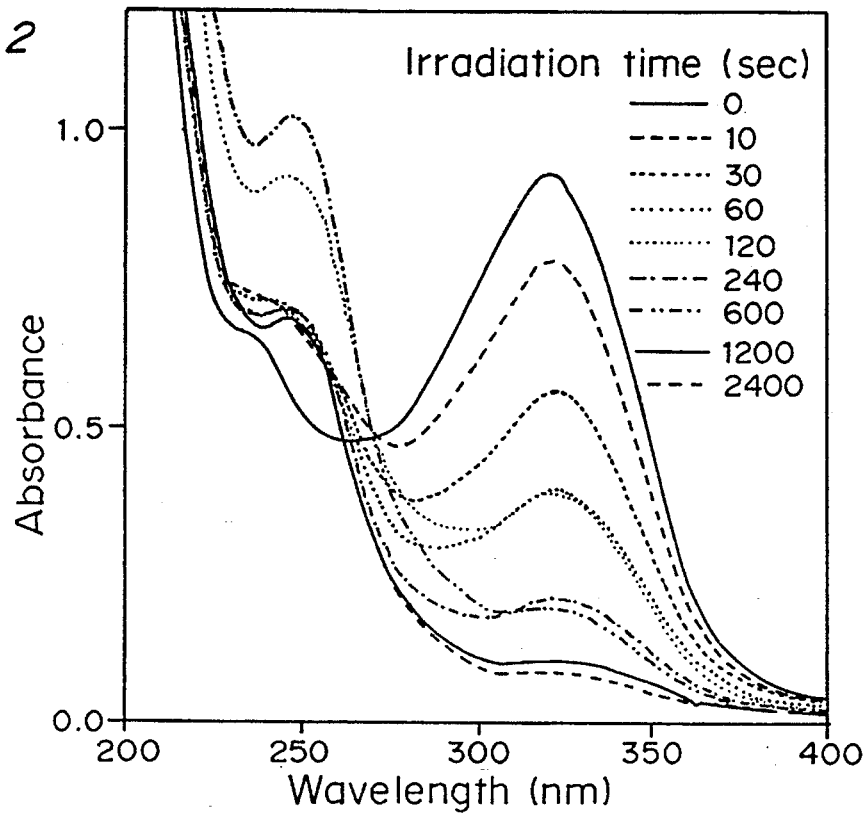
FIG. 2 is a graph of the effect of UV irradiation in time (seconds) on the UV absorption of $[NP\{OC_6H_5\}_1\{OC_6H_4CH=CHO(O)C_6H_5\}_1]_n$, referred to as polymer 8.
Figure 3:
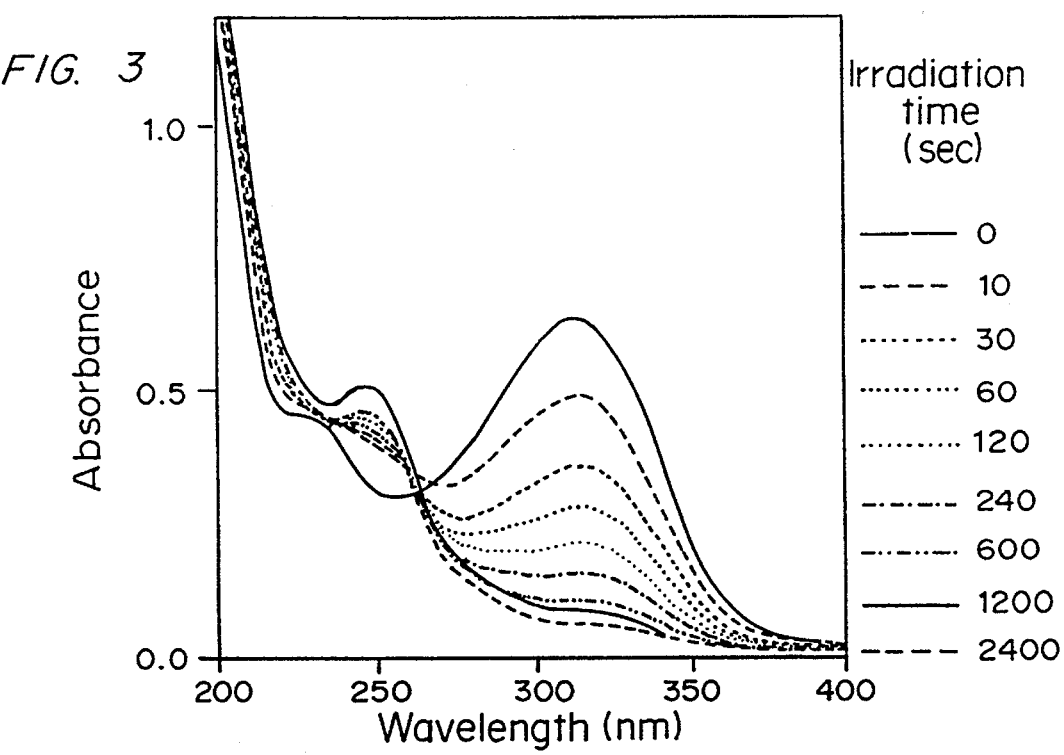
FIG. 3 is a graph of the effect of UV irradiation in time (seconds) on the UV absorption of $[Np\{OCH_2CF_3\}_{0.93}\{OC_6H_4CH=CHC(O)C_6H_5\}_{1.07}]n$, referred to as polymer 7.

The photolytic cross-linking of polymers 6–8 was followed by UV spectroscopy (see FIGS. 1–3). FIG. 1 indicates the effect of UV radiation on polymer 6. Immediately apparent is the decrease of the absorbance at 320 nm, attributed to a UV-induced 2+2 cycloaddition reaction. Also evident is a small increase in the absorbance at 244 nm due to the cis form of the chalcone group arising from cis-trans isomerization. However, the predominant reaction is cross-linking as shown by the greater change in the 320 nm absorption and the insolubility of polymers 6–8 in common organic solvents.

Photochemical cross-linking was monitored by measuring the relative intensity of the 320 nm absorption. It was found that, after a total of ten minutes exposure to UV light, the absorption corresponding to the carbon-carbon double bond alpha to the carbonyl at 320 nm had decreased in intensity to approximately 10–30% of the initial value.

Figure 4:
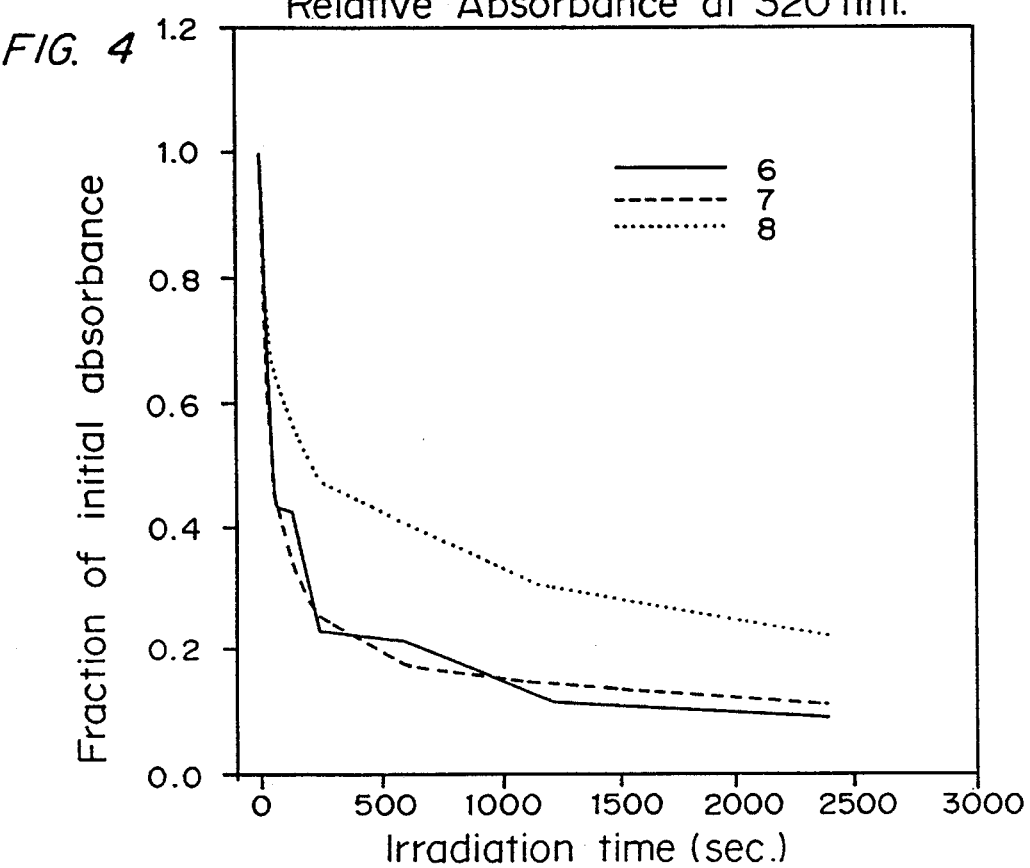
FIG. 4 is a graph indicating the relative absorbances at 320 nm over irradiation time (seconds) of polymers 6, 7 and 8.

Also, the relative sensitivity of the polymers [NP{OC$_6$H$_4$CH=CHC(O)C$_6$H$_5$}$_2$]$_n$6, [NP{OCH$_2$CF$_3$}$_{0.93}${OC$_6$H$_4$CH=CH(O)C$_6$H$_5$}$_{1.07}$]n 7 and [NP{OC$_6$H$_5$}$_1${OC$_6$H$_4$ CH=CHO(O)C$_6$H$_5$}$_1$]$_n$8 were studied by comparing the UV absorbances at 320 nm versus irradiation time (see FIG. 4). Minimal differences were found between 7 and 8. Polymer 6 was found to be the least sensitive to UV irradiation, with the absorbance reaching a plateau at 30% of the initial absorption.

Attempts to sensitize polymer 6 with 4-nitrophenol and 4-nitroanisole yielded only a modest increase in the rate of photocrosslinking.

EXAMPLE 9

Irradiation Of Trimer 2

The photo-cross-linking reaction of chalcone polymers 6–8 can be understood in terms of intermolecular 2+2 cycloaddition reactions. These reactions were modeled by the irradiation of a small-molecule chalcone-chlorophosphazene species, 2, and its cyclodimerization to form species 10.

The UV induced 2+2 cycloaddition reaction of cyclic trimers that bear the chalcone side group was investigated by the irradiation of trimer 2 with a medium-pressure H$_g$ lamp as shown in Scheme 3.

Scheme 3

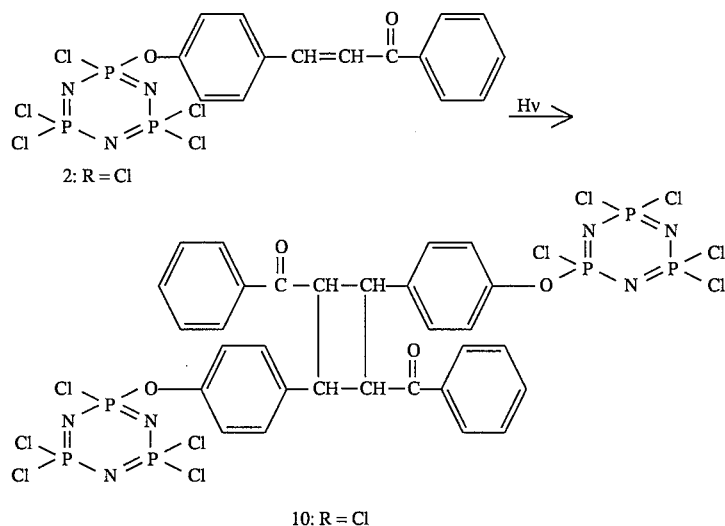

2: R = Cl

10: R = Cl

Scheme 3: Irradiation of Trimer 2

Trimer 2 (100 mg) was irradiated in the solid state from a distance of approximately 7 cm from an unfiltered 450 W Hanovia ultraviolet light source in air for approximately 7 hours, during which time a decrease occurred in the absorbance in the region of 305 nm, with concurrent formation of a mixture of dimers 10a and 10b. Dimer 10 was isolated by preparative TLC (silica gel substrate, 10% EtOAc/Hexane). $^{31}$P NMR (CDCl$_3$, 146 MHz) AM$_2$ V$_A$=12.7 ppm., v$_B$=23.1 ppm; $^1$H NMR (300 MHz CDCl$_3$) δ 7.8– 7.0 (m, 18 H), 5.05–4.75 (m, 4 H). MS, m/z calcd 1071 m/z found 1072 (+FAB).

Positive FAB mass spectrometry detected the molecular ion MH+ at 1071 mass units which matches the masses of the expected cyclobutane-type dimers. The mass spectrum of the mixture showed no evidence of open-chain (non-cyclobutane) saturated species (M+=1073). The $^1$H NMR spectrum of the Mixture, which showed several symmetrical multiples in the region of 3.9–5.0 ppm, is consistent with the formation of isomers 10a and 10b.

The UV spectra of trimers 3, 4 and 5 were also studied. UV absorption experiments indicated a λmax of trimers 2 and 4 is attributed to the withdrawal of electrons by the chloro and the trifluoroethoxy ligands in 2 and 4, respectively.

C. Preparation of Cinnamate Substituted Polyphosphazene Trimers

Cyclic trimeric phosphazenes were used as reaction models for the high polymers. Synthetic routes for the production of these compounds are shown in Schemes 4 and 5. t,340
Scheme 4: Synthesis of Trimer 14

Scheme 5

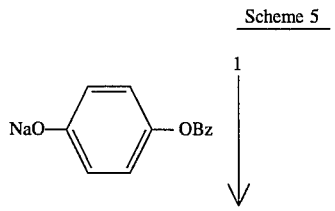

-continued
Scheme 5

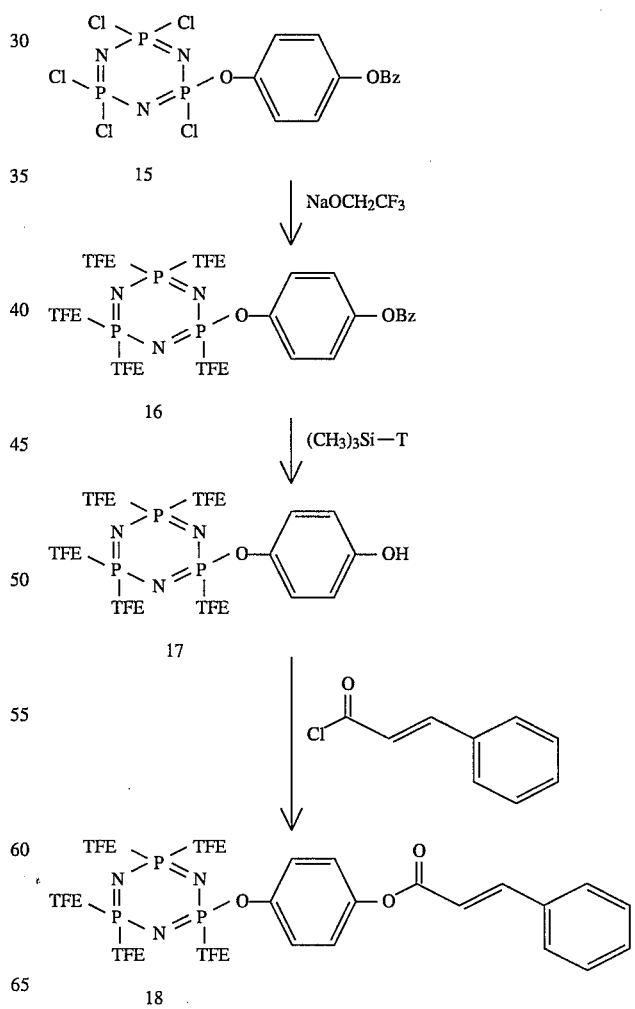

Scheme 5: Synthesis of Trimer 18

Hexasubstituted cyclic trimers 21 and 24 were used to model high polymers 32 and 35 where each phosphorous atom bears two photoactive groups.

In the synthesis of trimers 14 and 18, hexachlorocyclotriphosphazene was first treated with either $NaOC_6H_4$-p-$OB_z$ or $NaO(CH_2CH_2O)_2THP$ (THP=tetrahydropyranyl) to yield the pentachloro derivative 11 or 16. The remaining five chlorine atoms per molecule were then replaced by treatment with $NaOCH_2CF_3$ to yield the fully substituted trimers 12 and 16. Trimer 12 was deprotected to the free alcohol $N_3P_3(OCH_2CF_3)_5O(CH_2CH_2O)_2H(13)$ with the use of PPTS (pyridinium-p-toluene sulfonate) in 95% ethanol. Trimer 16 required the use of iodotrimethylsilane followed by hydrolysis of the resulting trimethylsilyl aryl ether with methanol to yield the free alcohol $N_3P_3(OCH_2CF_3)_5OC_6H_4OH$. Both trimers were esterified in pyridine solution with a slight excess of cinnamoyl chloride overnight at room temperature to yield cinnamate-substituted trimers 14 and 18.

The fully substituted trimers 21 and 24 required slightly different synthetic routes due to the nature and steric bulk of the side groups. Trimer 19 was synthesized from hexachlorocyclotriphosphazene 1 and eight equivalents of $NaOC_6H_4$-p-$OB_z$. This species was deprotected with $BBr_3$ to yield the hexahydroxy compound $[NP(OC_6H_4$-p-$OH)_2]_3$ 20, which was esterified with cinnamoyl chloride as described above.

Trimer 22 was synthesized in a manner analogous to trimer 19. Deprotection to yield the hexahydroxy compound 23 was accomplished with the use of HCl in ethanol to cleave the tetrahydropyranyl ether and give the trimer $[NP(O(CH_2CH_2O)_2H)_2]_3$. This trimer was esterified as described above to give $[NP(O(CH_2CH_2O)_2C(O)CH=CHC_6H_5)_2]_3$ 24.

EXAMPLE 10

Preparation of $N_3P_3Cl_5(OCH_2CH_2)_2OTHP$ 11

$H(OCH_2CH_2)OTHP$ (1.63 g, 858 mmol) was added to NaH (0.34 g, 14.2 mmol) in THF (50 mL) and the mixture was stirred overnight at room temperature. This solution was added dropwise over 15 minutes to 1 (3.0 g, 8.58 mmol) in THF (25 mL) with stirring, followed by stirring overnight at room temperature. Trimer 11 was used directly in the synthesis of 3. $^{31}$P NMR $AX_2$, $v_A$ =15.9, $v_B$=23.2 ppm, $J^{PNP}$=64 Hz.

EXAMPLE 11

Preparation of $N_3P_3(OCH_2CF_3)_5\{(OCH_2CH_2)_2OTHP\}12$

The reaction mixture produced in Example 10 was cooled to −78° C., $NaOCH_2CF_3$ (from $HOCH_2CF_3$(5.17 g, 51.7 mmol), sodium (1.4 g, 61 mmol) and THF (30 mL)) was added dropwise and the reaction was slowly allowed to warm to room temperature. The solvent was removed by rotary evaporation, $CH_2Cl_2$(150 mL) was added, and the organic layer was washed with water (3×100 mL). The organic layer was dried ($MgSO_4$) and the solvent was removed by rotary evaporation. The residue was purified by column chromatography (silica, 1:3 ether:hexane) to give trimer 12. $^{31}$NMR $(CDCl_3)AB_2$, 17.7 ppm,m; $^1$H NMR $(CDCl_3)$ δ 4.6(t,1 H), 4.30(m, 10 H), 4.1(q, 2 H), 3.85 (m, 2 H), 3.75 (m, 2 H), 3.50–3.65 (m, 2 H), 1.45–1.90 (m, 6 H).

EXAMPLE 12

Preparation of $N_3P_3(OCH_2CF_3)_5\{(OCH_2CH_2)_2OH\}13$

Trimer 3 (2.10 g, 2.56 mmol) was dissolved in 95% ethanol (50 mL), and PPTS (0.064 g, 0.25 mmol) was added and the mixture was stirred at room temperature. The solvent was removed by rotary evaporation and the volatiles removed under high vacuum. Confirmation of deprotection was accomplished by establishing the absence of the protecting group signals in the $^1$H NMR spectrum. $^{31}$P NMR $AB_2$, 19.4–21.6 ppm.

EXAMPLE 13

Preparation of $N_3P_3(OCH_2CF_3)_5\{(OCH_2CH_2)_2OC(O)CH=CHPh\}14$

Trimer 13 (1.80 g, 2.45 mmol) was dissolved in anhydrous pyridine (50 mL) and PhCH=CHC(O)Cl(0.61 g, 3.68 mmol) was added. The reaction mixture was stirred overnight at room temperature. The solvent was removed under vacuum, water (50 mL) was added, and the mixture was extracted with $CH_2Cl_2$ (3×50 mL). The organic layer was dried ($MgSL_4$) and the solvent was removed under reduced pressure. Column chromatography (silica, 10% EtOAc/hexane) was used to isolate pure 14. $^{31}$P NMR $AB_2$, 16.3–18.5 ppm; $^1$H NMR $(CDCl_3)$ δ 7.7 (d, 1 H, J=16 Hz), 7.5 (m, 2 H), 7.4 (m, 3 H), 6.5 (d, 1 H, J=16 Hz), 4.2–4.4 (m, 12 H), 4.1 (m,2 H), 3.8 (m, 4 H). MS m/z calcd 865, found, 866 (MH$^+$, +FAB).

EXAMPLE 14

Preparation of $N_3P_3Cl_5\{OC_6H_4$p-OBz$\}15$

Solid $HOC_6H_4$p-OBz (1.55 g., 7.75 mmol) was added to NaH (0.182 g, 7.6 mmol) in THF (60 mL) and the mixture was stirred for three hours. This solution was added to $[NPCl_2]_3$ in THF (25 mL) and the mixture was stirred warm overnight. The solvent was removed by rotary evaporation, ether (50 mL) was added, and the solution was washed with water (3×30 mL), dried ($MgSO_4$). The solvent was removed by rotary evaporation. Warming under vacuum removed residual $[NPCl_2]_3$. Yield: 3.08 g. (78%). $^{31}$P NMR $AX_2$, $v_A$=13.8 ppm, $v_B$=23.2 ppm, $J_{AB}$=58 Hz; $^1$H NMR$(CDCl_3)$δ 7.4 , (m, 5 H), 7.2, (d,2 H), 6.9, (d,2 H), 5.05 (s,2 H). MS, m/z calcd 509, found, 512 (CI), (M+2) H$^+$.

EXAMPLE 15

Preparation of $N_3P_3(OCH_2CF_3)_5\{OC_6H_4$-p-OBz$\}16$ 2,2,2-Trifluoroethanol (4.80 g. , 48 mmol) was added to sodium metal (1.10 g, 48 mmol) in THF (40 mL) and the mixture was stirred overnight at room temperature. This solution was added over one hour to a solution of 15 in THF (25 mL) at −78° C. and was then allowed to warm slowly to room temperature before being stirred overnight at room temperature. The solvent was removed by rotary evaporation, the solids were dissolved in ether (100 mL) and washed with water (3×50 mL). The organic layer was dried ($MgSO_4$) and the solvent removed by rotary evaporation. The beige solid was purified by removing $[NP(OCH_2CF_3)_2]_3$ by vacuum distillation. MS, m/z calcd 829, m/z found 830 (MH$^+$, CI). $^1$H NMR $(CDCl_3)$ δ 7.4(m,5 H), 7.1(d,2 H), 6.9(d,2 H), 5.0(s,2 H), 4.4(q,2 H), 4.35(m,4 H), 3.8(m,4 H); $^{31}$P NMR$(CDCl_3)AB_2$, $v_A$=18.0, $v_B$=14.9 pm, $J_{PNP}$=90 Hz.

EXAMPLE 16

Preparation of $N_3P_3(OCH_2CF_3)_5\{OC_6H_4p\text{-}OH\}$ 17

A solution of 16 (0.50 g, 0.30 mmol) in $CH_2Cl_2$ (30 mL) and $(CH_3)_3SiI$(0.36 g, 1.80 mmol, 3 equiv.) was heated to reflux for eight days. The reaction was allowed to cool to room temperature and methanol (2 mL) was added slowly. The solvent was removed by rotary evaporation and the solid purified by column chromatography (silica, 2:3 EtOAc:hexane). $^{31}P$ NMR $(CDCl_3)AB_2$, $v_A=14.4$, $v_B=17.5$ ppm; $^1H$ NMR$(CDCl_3)$ δ 7.1(d,2 H), 6.8(d,2 H), 4.4(q,2 H), 4.2(m,4 H), 3.85(m,4 H). MS, m/z calcd 739, m/z found 740 (MH+), (+FAB).

EXAMPLE 17

Preparation of $N_3P_3(OCH_2CF_3)_5\{OC_6H_4p\text{-}OC(O)CH\!\!=\!\!CHPh\}$ 18

A solution of trimer 17 (0.18 g, 0.24 mmol) and PhCH=CHC(O)Cl (0.018 g., 0.48 mmol) in pyridine (20 mL) was stirred at room temperature for four days. The solvent was removed under vacuum and the product was purified by preparative TLC (1:4 EtOAc:hexane). Further purification to remove $N_3P_3(OCH_2CF_3)_4(OC_6H_4p\text{-}OC(O)CH\!\!=\!\!CHPh)_2$ was not possible. MS, m/z calcd 869, m/z found 870 (+FAB, MH+).

EXAMPLE 18

Preparation of $[NP(OC_6H_4p\text{-}OBz)_2]_3$ 19

To a solution of $NaOC_6H_4$-p-OBz (prepared from 6.89 g, 34.4 mmol of $HOC_6H_4p$-OBz and NaH (0.82 g, 34.4 mmol)) in THF (100 mL) was added solid $[NPCl_2]_3$. The solution was heated to reflux overnight. The reaction mixture was allowed to cool, the solvent was removed by rotary evaporation and the residue was extracted with boiling water (4×250 mL). The solid was recrystallized from 1:1 THF-;hexane to yield beige needles. $^{31}P$ NMR δ +11,s; $^1H$ NMR$(CDCl_3)$ δ 7.35(m,30 H), 6.8(m,24 H), 4.95(s,12 H); $^{13}C$ NMR$(CDCl_3)$ δ 155.7, 144.4, 128.5, 128.0, 127.4, 121.9, 115.3, 70.4 MS, m/z calcd 1330, m/z found 1331 (+FAB), (MH+).

EXAMPLE 19

Preparation of $[NP(OC_6H_4p\text{-}OH)_2]_3$ 20

Trimer 19 (1.0 g, 0.75 mmol) was dissolved in $CH_2Cl_2$ (30 mL) and $BBr_3$ (6.0 mL of a 1M solution in $CH_2Cl_2$, 6 mmol) was added over 5 minutes with the formation of a heavy precipitate. The mixture was stirred for 30 minutes and then methanol (10 mL) was added slowly. The solvent was removed by rotary evaporation and dried under vacuum for 24 hours and used directly in the synthesis of 21. MS, m/z calcd 789, m/z found 790 (+FAB), (MH+).

EXAMPLE 20

Preparation of $[NP(OC_6H_4p\text{-}OC(O)CH\!\!=\!\!CHPh)_2]_3$ 21

Trimer 20 was dissolved in anhydrous pyridine (75 mL) and PhCH=CHC(O)Cl(0.91 g, 5.5 mmol) was added. The mixture was stirred at room temperature for 5 days. Most of the solvent was removed under vacuum and water (200 mL) was added to precipitate trimer 21. Recrystallization from THF/hexane gave a beige powder. $^1H$ NMR$(CDCl_3)$ δ 7.84(d,6 H,J=16 Hz), 7.5 (m,12 H), 7.35(m,18 H), 7.05 (m,24 H), 6.60(d,6 H,J=16 Hz); $^{31}P$ NMR$(CDCl_3)$ δ 9.9,s; $^{13}C$ NMR$(CDCl_3)$ δ 165.1, 147.7, 146.5, 134.1, 131.2, 128.9, 128.2, 122.7, 121.8, 117.2. MS, m/z calcd 1570, m/z found 1571 (+FAB, MH+). Anal. Calcd for $C_{90}H_{66}N_3O_{18}P_3$: C, 68.83; H,4.23; N, 2.68. Found, C,67.60; H:,4.18, N, 2.23.

EXAMPLE 21

Preparation of $[NP\{OCH_2CH_2)_2OTHP\}_2]_3$ 22

$H(OCH_2CH_2)_2OTHP$ (4.36 g, 23.1 mmol) was added to NaH (60%, 0.91 g) in THF (50 mL) and the mixture was stirred overnight at room temperature. Solid $[NPCl_2]_3$ (1.0 g, 2.8 mmol) was then added and the reaction mixture was stirred at room temperature for three days at room temperature. The solvent was removed by rotary evaporation, water (100 mL) added, and the aqueous layer was extracted with $CH_2Cl_2$(3×50 mL). The organic layer was dried $(MgSO_4)$ and the solvent removed by rotary evaporation. Column chromatography (10% $MeOH/CHCl_3$) isolated pure 22. $^{31}P$ NMR$(CDCl_3)$ δ 18.6,s; $^1H$ NMR$(CDCl_3)$ δ 4.6(t,6 H), 4.05(m,12 H), 3.9(m,12 H), 3.75–3.40 (m,36 H), 1.9–1.45(m,36 H); $^{13}C$ NMR$(CDCl_3)$ δ 98.9, 70.5, 70.0 (m), 66.6, 65.0, 62.2, 30.5, 25.4, 19.5.

EXAMPLE 22

Preparation of $[NP\{OCH_2CH_2)_2OH\}_2]_3$ 23

Trimer 22 (3.50 g, 2.75 mmol) was dissolved in methanol (100 mL) and 0.5 mL con. HCl was added, and the reaction mixture was stirred for three days at room temperature. The solvent was removed by rotary evaporation and the oil was dried overnight under high vacuum. $^{13}C$ NMR δ 72.3 (m), 69.3, 64.7, 60.2 (m); $^1H$ NMR (ace-$d_6$) δ 3.9 (br, 2 H), 3.6(m,4 H), 3.3–3.5 (m 4 H); $^{31}P$ NMR δ 19.2,s.

EXAMPLE 23

Preparation of $[NP\{OCH_2CH_2)_2OC(O)CH\!\!=\!\!CHPh\}_2]_3$ 24

Trimer 23 (2.10 g, 2.75 mmol) and PhCH=CHC(O)Cl (3.66 g, 22.0 mmol) were dissolved in anhydrous pyridine (75 mL) and were stirred for 3 days at room temperature. The solvent was removed under vacuum, water (100 mL) added, and the aqueous layer was extracted with $CH_2Cl_2$(4× 50 mL). The organic layer was dried $(MgSO_4)$ and the solvent was removed by rotary evaporation. The remaining oil was purified by column chromatography (5% MeOH/ $CH_2Cl_2$, silica) $^{31}P$ NMR δ 18.6,s; $^1H$ NMR δ 7.7 (d, 1 H, J=16 Hz), 7.5 (m, 2 H), 7.4 (m, 3 H), 6.45 (d, 1 H, J=16 Hz), 4.35 (m, 2 H), 4.1 (br, 2 H), 3.75 (m, 6 H). MS, m/z calcd 1547, m/z found 1548 (+FAB, MH+).

D. Preparation of Cinnamate Bearing Polyphosphazene Polymers

An example of one synthetic pathways to polymers 29 and 33 are depicted in Scheme 6.

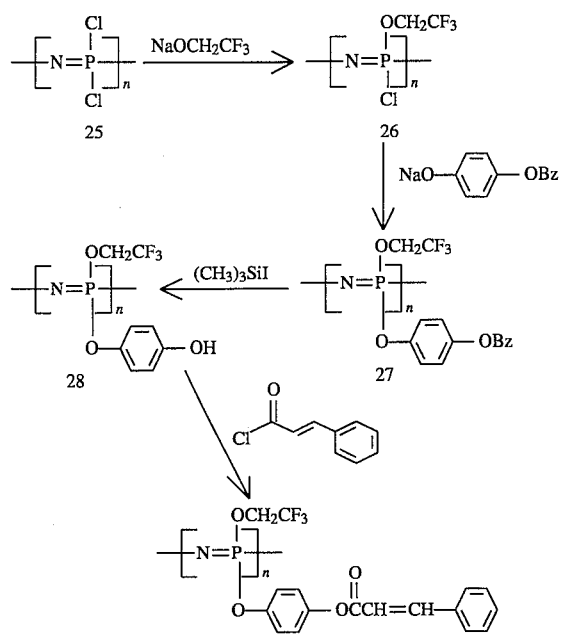

Scheme 6: Preparation of Polymer 29

Poly(dichlorophosphazene) 25 was prepared by the thermal ring opening polymerization of 1. Trifluoroethoxy cosubstituent polymer 26 was prepared by allowing a stoichiometric deficiency of NaOCH$_2$CF$_3$ to react with polymer 25. The remaining P—Cl reactive sites were replaced by the use of NaOC$_6$H$_4$-p-OB$_z$ to give fully substituted polymer 29.

Polymer 31 was prepared in a slightly different manner, by the addition of sodium trifluoroethoxide nucleophile last (see Scheme 7).

Scheme 7: Preparation of Polymer 31

Single substituent polymers [NP(OC$_6$H$_4$OB$_z$)$_2$]$_n$ (37) and [NP(O(CH$_2$CH$_2$O)$_2$THP)$_2$]$_n$ (34) were synthesized by the reaction of macromolecular intermediate 25 with NaOC$_6$H$_4$-p-OB$_z$ and NaO(CH$_2$CH$_2$O)$_2$THP.

Polymers 31 and 34, bearing the THP ether protecting group, were deprotected to the free hydroxyl polymers 32 and 35, respectively, with the use of PPTS in 95% ethanol solution.

The initial reagent explored to bring about the cleavage of the benzylic ether to obtain hydroxy-substituted polymers was BBr$_3$. In both homopolymer 37 and trifluoroethoxy cosubstituent polymer 27, BBr$_3$ afforded nearly complete deprotection to the free hydroxy group to give polymers 38 and 28. However, the conditions (30 minutes with a slight excess of BBr$_3$ at room temperature) resulted in a noticeable molecular weight decline, especially with trifluoroethoxy cosubstituent polymer 27, as estimated by the viscosity of THF solutions. Similar results were obtained when the trifluoroethoxy cosubstituent polymer was deprotected for five minutes at room temperature. It is speculated that the molecular weight decline results from the lone pair of electrons on the backbone nitrogen atoms coordinating to the boron atom and leading to backbone scission.

Therefore, the use of B-bromo-9-BBN (9-bromo-9-borabicyclo[3.3.1]nonane), a milder and much more sterically hindered reagent for the cleavage of benzyl ethers than BBr$_3$, was attempted for the deprotection reaction. This reagent was used in the anticipation that a more sterically crowded environment would allow the deprotection reaction to occur, while retarding the lone pair coordination which may lead to backbone degradation. The level of deprotection of both the trifluoroethoxy cosubstituent polymer 27 and homopolymer 37 was so low as to be undetectable by $^1$H NMR even in the presence of more than of 10 equivalents of B-Bromo-9-BBN.

The last deprotection reagent investigated was iodotrimethylsilane. This reagent provided almost full deprotection of the trifluoroethoxy cosubstituent polymer 27 without the

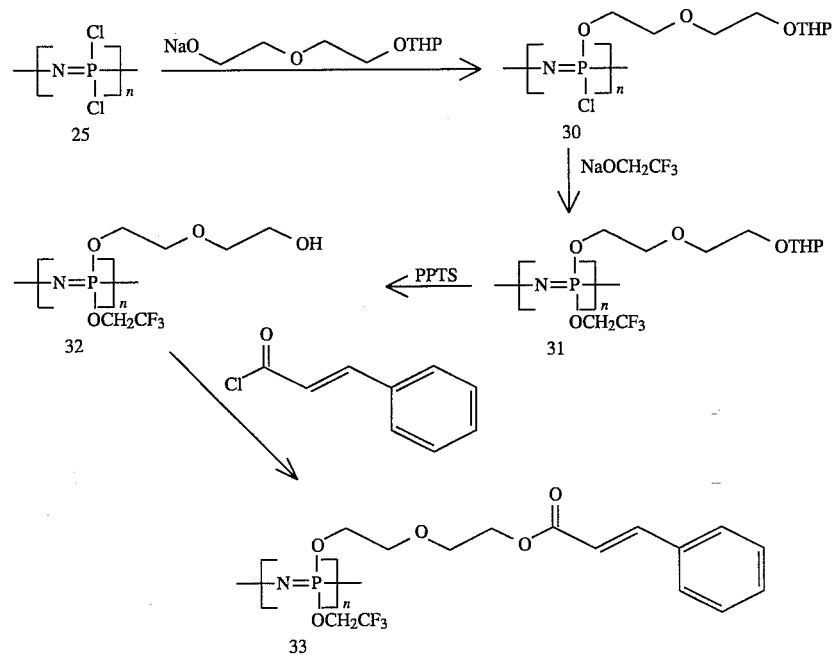

catastrophic molecular weight degradation that occurred with the use of BBr$_3$. However, in contrast to the trifluoroethoxy cosubstituent polymer, homopolymer 37 was completely unaffected by iodotrimethylsilane. This may be due to the steric crowding around the reactive Si—I bond which prevents the reaction between the sterically more demanding benzyloxyphenoxy homopolymer, than in the case of the smaller trifluoroethoxy cosubstituent.

The only reagent to fully deprotect homopolymer 37 is the relatively harsh reagent BBr$_3$. Backbone degradation was minimized by short (five minute) reaction times rather than the initially long times (thirty minutes).

EXAMPLE 24

Preparation of [NP(PCH$_2$CF$_3$)$_1$(OC$_6$H$_4$-p-OBz)$_1$]$_n$ 27

Poly(dichlorophosphazene) 25 (5.0 g, 43 mmol) was dissolved in warm dioxane (700 mL) overnight with stirring. 2,2,2-Trifluoroethanol (4.31 g, 43.1 mmol) was added to sodium metal (1.05 g, 45.7 mmol) in dioxane (100 mL) and HOC$_6$H$_{4p}$-OBz (2.6 g, 13.0 mmol) was added to NaH in dioxane and stirred overnight at room temperature. The solution of 2,2,2-trifluoroethoxide was added to the polymer solution and was stirred and warmed overnight. Finally, the solution of NaOC$_6$H$_4$-p-OBz was added to the partially substituted polymer and the solution was heated at reflux for five days. The solvent was removed by rotary evaporation and the solution was poured slowly into water (4 L). Further purification was accomplished by additional precipitations of THF solutions into water (4 times total), iPrOH (2 times) and hexane (1 time). Yield: 9.8 g. (66%). $^{31}$P NMR δ -17.6; $^1$H NMR(CDCl$_3$) δ 7.25 (5H, br), 6.4–7.0 (4 H, br), 4.6 (br, 2 H), 3.75 (br, 2 H).

EXAMPLE 25

Preparation of [NP(OCH$_2$CH$_3$)$_1$(OC$_6$H$_4$p-OH)$_1$]$_n$ 28

Polymer 27 (0.50 g, 1.46 mmol) was dissolved in dry CH$_2$Cl$_2$(100 mL) and (CH3)$_3$SiI (1.46 g, 7.3 mmol) was added. The mixture was heated at reflux for 3 days. Methanol (4 mL) was added at reflux and the solvent was decanted from the precipitated polymer. Further solvent removal was achieved by vacuum drying overnight. $^1$H NMR(CDCl$_3$) δ 6.9 (2 H, br), 6.6 (2 H, br), 4.1 (2 H, br).

EXAMPLE 26

Preparation of [NP(OCH$_2$CF$_3$)$_1$(OC$_6$H$_4$p-OC(O)CH=CHPh)$_1$]$_n$ 29

Polymer 28 (0.37 g, 1.46 mmol) was dissolved in anhydrous pyridine (100 mL) and PhCH=CHC(O)Cl (0.24 g, 1.44 mmol) was added and the solution stirred overnight at room temperature. Most of the solvent was removed under vacuum and water (100 mL) was added to precipitate the polymer. Further purification was accomplished by precipitation of THF solutions of 29 into water. $^{31}$p NMR δ -17.65, br; $^1$H NMR(CDCl$_3$) δ 8.25 (br, 1 H), 7.7 (br, 2 H), 7.4 (br, 2 H), 7.0 (br, 4 H), 6.7 (br, 2 H), 4.25 (br, 2 H). Anal. Calcd: C, 50.15; H, 3.65; N, 3.90. Cl, O. Found: C, 50.00; H, 3.50; N, 4.42; Cl, 0.022.

EXAMPLE 27

Preparation of [NP(OCH$_2$CH$_3$)$_1${(OCH$_2$CH$_2$)$_2$OTHP}$_1$]$_n$ 31

Poly(dichlorophosphazene) 25 was dissolved in THF (400 mL) overnight with stirring. H(OCH$_2$CH$_2$)$_2$OTHP (3.93 g, 20.7 mmol) was added to NaH (60%, 0.83 g) in THF (50 mL). 2,2,2-Trifluoroethanol (1.72 g, 17.2 mmol) was added to Na (0.40 g, 17.4 mmol) in THF (50 mL). The mixture was stirred overnight at room temperature. The THF solution of NaOCH$_2$CH$_3$ was added to 25 and stirred warm overnight. Na(OCH$_2$CH$_2$)$_2$OTHP was added to the polymer solution and stirred warm for 2 days. The solution was concentrated by rotary evaporation and the polymer precipitated by pouring into wager. Two additional precipitations from THF into water yielded pure 31. Yield: 5.6 g. (98%). $^{31}$P NMR δ -6.5, br; $^1$H NMR(CDCl$_3$) δ 4.6 (br, 1 H), 4.3 (br, 2 H), 4.1 (br, 2 H), 3.8 (br, 4 H), 3.7–3.4 (br, 4 H), 1.9–1.0 (br, 6 H).

EXAMPLE 28

Preparation of [NP(OCH$_2$CH$_3$)$_1${(OCH$_2$CH$_2$)$_2$OH}$_1$]$_n$ 32

Polymer 31 (2.0 g, 6.0 mmol) was dissolved in ethanol (100 mL), PPTS (1.50 g, 6.0 mmol) was added and the reaction stirred warm for 5 days. Dialysis against water (8 days) then methanol (7 days), rotary evaporation of the solvent and then vacuum drying yielded pure 32. $^{31}$P NMR δ -4.9, -6.3; $^1$H NMR: 4.5 (2 H, br), 4.2 (br, 2 H), 4.0–3.5 (br, 6 H), 2.85 (br, 1 H).

EXAMPLE 29

Preparation of [NP(OCH$_2$CF$_3$)$_1${(OCH$_2$CH$_2$)$_2$—OC(O)CH=CHPh}$_1$]$_n$ 33

Polymer 33 was prepared using the method set forth in Example 26, with the reagents and quantities as follows. 32: 1.2 g, 4.8 mmol. Pyridine: 75 mL. PhCH=CHC(O)Cl:0.96 g, 5.8 mmol. $^{31}$P NMR δ-6.1, -7.3; $^1$H NMR δ 7.65 (d, 1 H, J=14 Hz), 7.5–7.3 (br, 5 H), 6.41 (d, 1 H, J=17 Hz), 4.3 (br, 4 H), 4.1 (br, 2 H), 3.7 (br, 4 H). Anal. Calcd: C, 47.5; H, 4.52; N, 3.69. Found: C, 47.05; H, 4.93; N, 3.59. T$_g$: −25° C. M$_w$=1.8×10$^5$, Mn=6.6×10$^5$.

EXAMPLE 30

Preparation of [NP{O(CH$_2$CH$_2$O)$_2$THP}$_2$]$_n$ 34

Polymer 33 was prepared using the method set forth in Example 26 with the reagents and quantities as follows. 25: 3.0 g, 26 mmol in THF (500 mL). HO(CH$_2$CH$_2$O)$_2$THP: 14.7 g, 77.6 mmol. NaH: 2.79 g, 69.8 mmol (60% dispersion in mineral oil) in THF (100 mL). $^{31}$P NMR δ -7.87; $^1$H NMR δ 4.6 (br, 1 H), 4.1–3.3 (br, 10 H), 1.7–1.0 (br, 6 H). $^{13}$C NMR δ 98.8, 66.6, 65.0, 62.0, 30.6, 25.5, 19.5.

EXAMPLE 31

Preparation of

[NP{O(CH$_2$CH$_2$O)$_2$H}$_n$ 35

Polymer 35 was prepared using the method set forth in Example 28 with the reagents and quantities as follows. 34: 1.2 g, 2.8 mmol. 95% EtOH: 100 mL. PPTS: 0.07 g, 0.28 mmol. $^{31}$P NMR δ -7.98; $^1$H NMR δ 4.16 (br, 1 H), 3.73–3.56 (m, 8 H); $^{13}$C NMR δ 74.3, 73.0, 67.3, 63.0.

EXAMPLE 32

Preparation of

[NP{O(CH$_2$CH$_2$O)$_2$C(O)CH=CHPh}$_2$]$_n$ 36

Polymer 36 was prepared using the method set forth in Example 26 with the reagents and quantities as follows. Polymer 35: 2.4 g, 9.4 mmol. Pyridine: 75 mL. PhCH=CHC(O)Cl:3.14 g, 18.9 mmol. $^1$H NMR δ 7.6 (d, 1 H, J=16 Hz), 7.4 (br, 2 H), 7.25 (br, 3 H), 6.4 (d, 1 H, J=16 Hz), 4.3 (br, 4 H), 4.1 (br, 2 H), 3.7 (br, 4 H); $^{31}$P NMR (CDCl$_3$) δ -7.4, s; $^{13}$C NMR(CDCl$_3$) δ 166.8, 145.0, 134.3, 130.2, 128.8, 128.2, 117.8, 70.3, 69.0, 65.1, 63.5. T$_g$: -16° C., Anal. Calcd:C, 58.65; H, 6.15; N, 2.85. Cl, O. Found: C, 59.35; H, 6.15; N, 2.46; Cl, <0.5. M$_w$=5.6×10$^4$, M$_n$=1.4× 10$^5$.

EXAMPLE 33

Preparation of

[NP(OC$_6$H$_4$p-OBz)$_2$]$_n$ 37

Polymer 37 was prepared using the method set forth in Example 24 with the reagents and quantities as follows. 25: 2.0 g. 1.7 mmol. Dioxane: 400 mL. HOC$_6$ H$_4$p-OBz:12.7 g, 6.4 mmol. NaH (60% dispersion in mineral oil): 1.52 g, all in dioxane (100 mL). Yield: 4.6 g. (65%).

EXAMPLE 34

Preparation of

[NP(OC$_6$ H$_4$p-OH)$_2$]$_n$ 38

Polymer 37 (0.50 g, 1.13 mmol) was dissolved in dry CH$_2$Cl$_2$(100 mL) overnight with stirring. BBr$_3$ (2.7 mL, 1M in CH$_2$Cl$_2$) was added and the reaction was stirred for 5 minutes at room temperature. Ethanol (3 mL) was added slowly, the solvent was decanted from the polymeric precipitate, and the polymer was dried under vacuum overnight. $^{31}$P NMR δ -16.1; $^{31}$C NMR(DMSO-d$_6$) δ 153.5, 121.6, 115.0, 95.4; $^1$H NMR(DMSO-d$_6$) δ 6.64 (br, 2 H), 6.31 (br, 2 H).

EXAMPLE 35

Preparation of

[NP(OC$_6$H$_4$p-OC(O)CH=CHPh)$_2$]$_n$ 39

Polymer 39 was prepared using the method set forth in Example 26 with the reagents and quantities as follows. 38: 0.29 g, 1.10 mmol. Pyridine: 75 mL. PhCH=CHC(O)Cl: 0.44 g, 2.64 mmol. $^{31}$P NMR δ -16.8, br; $^1$H NMR δ 6.4–7.6, br. Anal. Calcd: C, 68.83; H, 4.24; N, 2.68; Cl, O. Found: C, 64.31; H, 4.06; N, 3.29, Cl, 0.0299 . T$_g$:59° C.

E. U.V. Absorption Studies of Cyclic Trimers and Polymers Substituted with Cinnamate Groups

EXAMPLE 36

Ultraviolet Absorption Studies of Cyclic Trimers.

The UV induced 2+2 cycloaddition reaction of cyclic trimers that bear cinnamate side groups was investigated by the irradiation of trimer 14 with a medium-pressure Hg lamp as shown in Scheme 8.

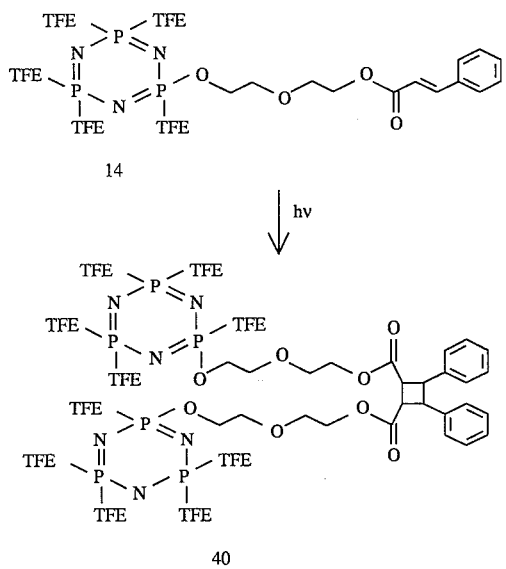

Scheme 8: Irradiation of Trimer 14

Trimer 14 has an absorption at 280 nm (CH$_2$Cl$_2$ solvent). Species 14 was irradiated in the solid state for two hours 10 cm from the UV lamp, to induce the formation of dimer 40. Dimer 40 was characterized in its impure form by $^{31}$P and $^1$H NMR spectroscopy, and mass spectrometry. Positive FAB mass spectrometry detected the protonated molecular ion MH+ at 1731 mass units, which matches the mass of the expected cyclobutane-type dimer. The mass spectrum showed no evidence of open-chain (non-cyclobutane) saturated species (M$^+$=1732). The $^1$H NMR spectrum of 40 consisted of two doublets (J=14 Hz) centered at 7.0 and 6.0 ppm, which, due to symmetry consideration, indicate the formation of dimer 40 with the phenyl groups in the Z configuration about the cyclobutane ring.

EXAMPLE 37

Ultraviolet Absorption of Polymers 36 and 39.

The ultraviolet absorption behavior of polymers 36 and 39 was investigated by UV spectroscopy. Thin films of polymers 36 and 39 were cast onto quartz plates from inhibitor-free THF and the solvent was removed under vacuum. The λ$_{max}$ for the cinnamate chromophore of both polymer 36 and polymer 39 was found to be at 276 nm which compares favorably to other similar aliphatic cinnamate esters.

EXAMPLE 38

Photolytic Cross-linking Behavior of Polymers 36 and 39

Figure 5:
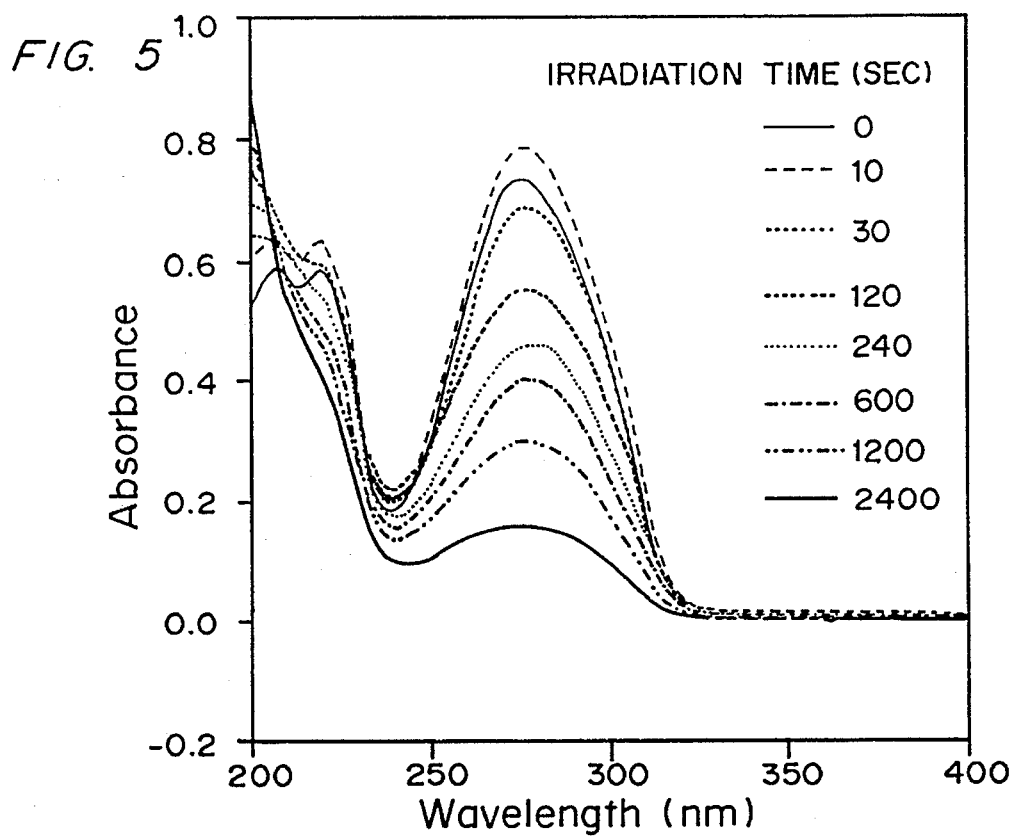
FIG. 5 is a graph of the effect of UV irradiation over time (seconds) on the UV absorption of $[NP\{O(CH_2CH_2O)_2C(O)CH=CHPh\}_2]_n$, referred to as polymer 36.

The photolyric cross-linking of polymer 36 was followed by UV spectroscopy, as shown in FIG. 5. The polymer film was irradiated with an unfiltered sunlamp UV source. The decrease in the 274 nm absorption was used to monitor the progress of crosslinking. The photocrosslinking presumably occurs mainly via the formation of cyclobutane-type dimers, perhaps accompanied by various free radical crosslinking reactions. Cross-linking was confirmed by the insolubility of polymer 36 in common organic solvents after irradiation.

Figure 6:
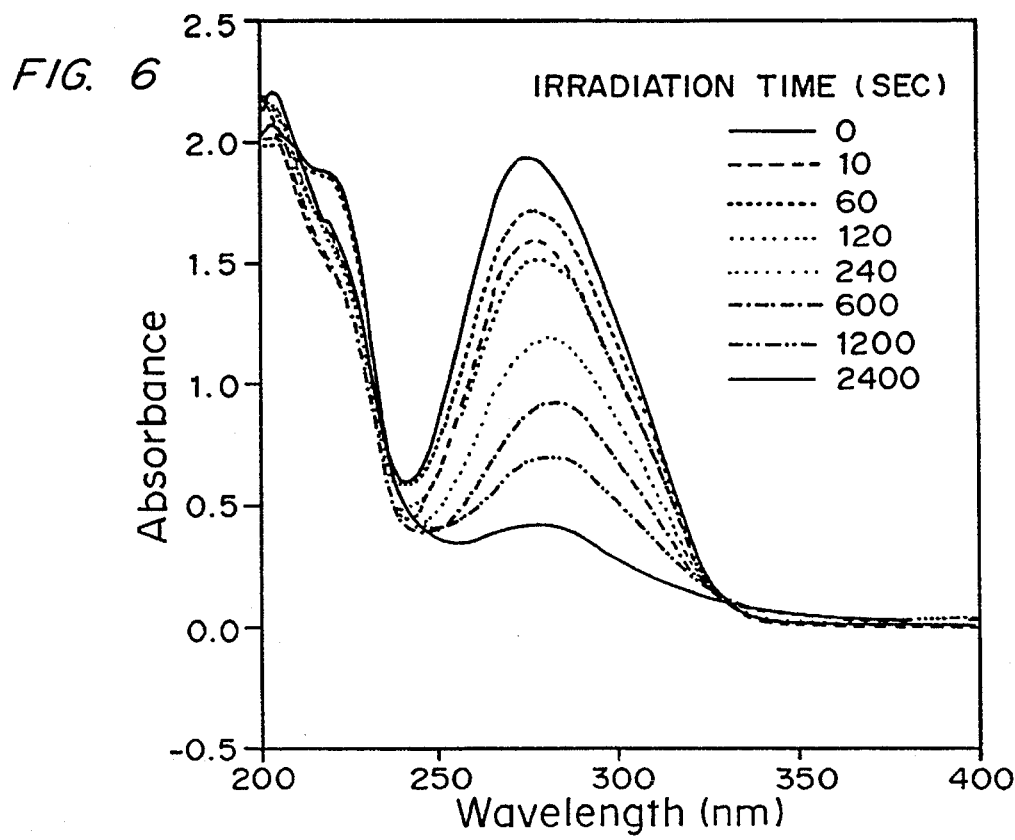
FIG. 6 is a graph of the effect of UV irradiation over time (seconds) on the UV absorption of $[NP(OC_6H_4p—OC(O)CH=CHPh)_2]_n$, referred to as polymer 39.

The photolytic crosslinking of polymer 39 was also followed by UV spectroscopy as shown in FIG. 6. As can be seen in FIG. 6, the photocrosslinking behavior and the $\lambda_{max}$ of polymer 39 are essentially identical to that of polymer 36. These results indicate a minimal influence on the crosslinking process by either the loading of the photoactive group or the type of spacer, respectively.

The polymers 27 and 30 undergo a photochemically induced 2+2 cycloaddition reaction to form a crosslinked matrix.

A lowering of molecular weight during the deprotection and esterification steps involving cinnamate bearing polyphosphazenes can be observed. This can be avoided by the derivatization of macromolecular intermediate 25 with the photoactive chalcone group, which has both synthetic advantages and higher Tg's.

An ideal photoresist has a glass transition temperature, significantly above room temperature and an even higher $T_g$ after crosslinking. Although polymer 39 has a $T_g$ of 59° C., and polymers 33 and 36 have $T_g$'s of −25° and −16° C., respectively, the photolytic crosslinking behavior of polymers 36 and 39 are very similar. This is consistent with a minimal influence of the $T_g$ on photocrosslinking behavior. However, the effectiveness of the crosslinking step raises the possibility that this system may be useful for the crosslinking of macromolecular surface coatings.

III. Encapsulation of Biologically Active Materials Using Polyphosphazenes

An area of recent interest is that of biocompatible semipermeable membranes that can be used to encapsulate living cells or other substances for implantation into humans and animals. An example of one important use of such membranes is the coating of insulin-producing cells which are transplanted into diabetic patients. The insulin-producing cells, provided by a human or animal donor, are encapsulated by a membrane which should protect them from attack by the immune system. A membrane is designed that is biocompatible and immunoprotective. The membrane should allow nutrients to pass out, but it should prevent the passage of immunoglobulins. Other applications include the controlled release of drugs and the microencapsulation of gases or other substances for use in biomedical imaging, as discussed in more detail below.

In a preferred mode, the polymers that encapsulate living cells in extremely small capsules (microspheres) have a large surface area to allow a good flow of nutrients and insulin.

Researchers at Biohybrid Technologies in Schrewsbury, Mass. have developed a method for the encapsulation of insulin-producing islets of Langerhans. The islets are encapsulated in alginate, a seaweed-derived polymer made up of guluronic and mannuronic acid segments. The islet-containing polymer microspheres are exposed to a solution containing a calcium salt, which causes spontaneous crosslinking. This ionic crosslinking process is reversible. The microspheres must then be coated with polylysine to prevent rejection by the immune system. However, polylysine itself stimulates the formation of fibrous tissue. The polylysine-coated alginate microspheres must therefore be coated with another layer, this one of guluronic acid-rich polylysine.

These resulting microspheres are injected into the abdominal wall of the patient, where they are bathed in a nutrient-rich fluid. The encapsulated islet cells respond to fluctuating levels of glucose in the same way that normal pancreatic islet cells would, by secreting insulin at different rates. This technique has been used successfully in dogs and one human patient.

It was desirable to improve the mechanical properties of the microspheres, which can break down easily during the injection process, by the introduction of photopolymerizable monomer groups into the alginate polymer. Upon exposure to light in the presence of a dye, the photopolymerizable groups covalently crosslink the alginate, thus providing biological activity for an extended period of time. This process improves the durability of the microsphere.

However, this method contains disadvantages. First, as noted above, the process for preparing the microcapsule is complex, requiring the formation of three separate layers to avoid attracting the immune system to the microsphere or causing the formation of fibrous materials around the implanted microsphere. The photocrosslinking discussed above also has drawbacks because the dye which is used to crosslink the alginate may be toxic.

The chalcone or cinnamate bearing polyphosphazenes described herein can be used in place of alginate polymers for the encapsulation of cells or other biologically active materials. A chalcone or cinnamate bearing polyphosphazene should be selected for encapsulation of cells that is stable, to allow a few repeat injections of cells, is easy to manufacture with controlled purity and high reproducibility, and should not promote the formation of fibrous tissue. The polymer must not decompose to toxic materials nor be rejected by the body. The encapsulation process should not cause significant damage to the living cells. The microspheres should be stable to the stresses encountered during injection into the patient; and the membrane should allow nutrients to pass, but should prevent the passage of immunoglobins.

In one embodiment, a cosubstituent phosphazene polymer is used to immobilize the cells or other biologically active materials. Polyphosphazenes that contain cinnamate or chalcone groups, or a mixture thereof (or other unsaturated group capable of crosslinking on exposure to UV irradiation), as well as substituent groups that bear carboxylic acid, sulfonic acid, hydroxyl, or other ionizable moieties that ionically crosslink when mixed with di or tri valent ions of opposite charge can be used for this purpose. Any ratio of substituent groups can be used that achieves a desired effect. A preferred copolymer system is a polyphosphazene copolymer of formula

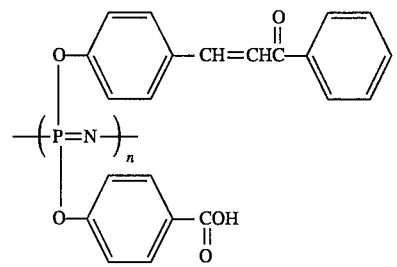

which contains phenoxycarboxylato and photocrosslinkable chalcone groups. The relative amounts of the two groups may be varied to provide a polymer with slightly different properties.

One embodiment of this preferred polymer is a copolymer having approximately 70, 80 or 90% carboxylato groups and the remaining percentage chalcone groups to provide desirable material properties. These polymers can be crosslinked through the carboxylato side groups by exposure to di- or trivalent cations and they can be further stabilized by exposure to low doses of UV radiation which result in covalent crosslinks of the chalcone groups.

The doubly-crosslinked polymers of the present invention are more stable than polymers crosslinked by only ionic crosslinks, and allow control over crosslink density by varying the amount of the chalcone or cinnamate groups in the polymers.

These copolymers also avoid the toxicity problem associated with the use of initiator dyes, which are not required for photosensitization. Furthermore, the present synthetic preparation yields a more reproducible product than other routes which rely on the use of natural products.

The resulting copolymers can be easily modified to result in biodegradable capsules for the delivery of a wide variety of substances, including biologically active materials. See for example, U.S. Pat. No. 5,053,451 (which discloses that poly(carboxylatophenoxy)phosphazene can be ionically crosslinked to form a hydrogel), and U.S. Pat. No. 5,149,543 (which discloses a composition that includes a biological material such as a liposome, virus, procaryotic cell, or eucaryotic cell encapsulated in an ionically crosslinked polyphosphazene or other polyelectrolyte), incorporated herein by reference.

IV. Preparation of Gas-filled Microbubbles Using Cinnamate or Chalcone Bearing Polyphosphazenes Polyphosphazenes that contain cinnamate or chalcone groups, or a mixture thereof (or other unsaturated group capable of crosslinking on exposure to UV irradiation), as well as substituent groups that bear carboxylic acid, sulfonic acid, hydroxyl, or other ionizable moieties that ionically crosslink when mixed with di or tri valent ions of opposite charge can be used to prepare gas-filled microbubbles. Divalent or trivalent pharmaceutically acceptable cations such as zinc, calcium, bismuth, barium, magnesium, aluminum, copper, cobalt, nickel, or cadmium, are preferred.

The synthetic polyphosphazenes are crosslinked in gasified solutions of ions of the opposite charge to encapsulate gaseous agents, including imaging contrast agents. The resulting product is a relatively homogenous population of spherical hydrogel gas-filled microcapsules. As used herein, a "microcapsule" refers to a spherical hydrogel gas-filled particle which may have one or more gas bubbles entrapped therein, and may have a liquid core of the same or different material as the hydrogel.

In one embodiment, the poly(organophosphazene) contains (i) ionized or ionizable pendant groups that contain, for example, carboxylic acid, sulfonic acid, or hydroxyl moieties, (ii) pendant groups that are susceptible to hydrolysis under the conditions of use, to impart biodegradability to the polymer, such as chlorine, amino acid, amino acid ester, imidazole, glycerol, and glucosyl, and (iii) a chalcone, cinnamate or other unsaturated group capable of crosslinking when irradiated. In a typical embodiment, a portion, generally 10% or less, of the side chain groups, are susceptible to hydrolysis.

It should be understood that certain groups, such as heteroaromatic groups other than imidazole, hydrolyze at an extremely slow rate under neutral aqueous conditions, such as that found in the blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer. While the ionizable groups are usually on nonhydrolyzable pendant groups, they can alternatively, or in combination, also be positioned on hydrolyzable groups.

Microbubbles, microspheres or microparticles prepared according to the present invention can be targeted to specific regions of the body by covalently binding to the polymer a targeting molecule. The targeting molecule can be, for example, a protein or peptide (such as a hormone, antibody, antibody fragment, such as the Fab or $Fab_2$ antibody fragments, or a specific cell surface receptor ligand), lipid, polysaccharide, nucleic acid, carbohydrate, a combination thereof, or other molecule, including a synthetic molecule, that identifies and localizes at the target material.

The microbubbles or microparticles can also be designed to minimize tissue adhesion by covalently binding a poly(alkylene glycol) moiety to the surface of the microbubble. The surface poly(alkylene glycol) moieties have a high affinity for water that reduces protein adsorption onto the surface of the particle. The recognition and uptake of the nanoparticle by the reticuloendothelial system (RES) is therefore reduced.

In one embodiment, the terminal hydroxyl group of the poly(alkylene glycol) can be used to covalently attach biologically active molecules, or molecules affecting the charge, lipophilicity or hydrophilicity of the particle, onto the surface of the particle. The biologically active molecule can be a protein, carbohydrate or polysaccharide, nucleic acid, lipid, a combination thereof, or a synthetic molecule, including organic and inorganic materials.

The method of preparing the microcapsules should be selected to provide a microcapsule having the desired size for the intended use. In a preferred embodiment for the preparation of injectable microcapsules capable of passing through the pulmonary capillary bed, the microcapsules should have a diameter of between approximately one and seven microns. Larger microcapsules may clog the pulmonary bed, and smaller microcapsules may not provide sufficient echogenicity. Larger microcapsules may be useful for administration routes other than injection, for example oral (for evaluation of the gastrointestinal tract) or by inhalation.

A. Preparation of a polymer solution.

In general, the polymer is dissolved or dispersed into a solution which is then sprayed into a solution of crosslinking counterions. This is typically an aqueous solution or dispersion that can include water-miscible organic solvents, including but not limited to dialkyl sulfoxides, such as dimethyl sulfoxide DMSO); dialkyl formamides, such as dimethyl formamide (DMF); $C_{1-5}$ alcohols, such as methanol and ethanol; ketones such as acetone and methyl ethyl ketone; and ethers such as tetrahydrofuran (THF), dibutyl ether and diethyl ether. The solution can be neutral, acidic or basic, and can contain salts or buffers. If the ionic polymer is insoluble in water, or insufficiently dispersible, the polymer can be converted to its conjugate acid or base that is typically more water soluble, and that conjugate acid or base then exposed to the di- or multivalent counterion for crosslinking.

B. Gases to be encapsulated

The ratio of polymer to gas is determined based on the gas that is to be encapsulated, for example, as required to produce a particle size small enough to be injected. Any desired inert gas can be incorporated into the polymeric materials at the time of hydrogel formation, including air, argon, nitrogen, carbon dioxide, nitrogen dioxide, methane, helium, neon, and oxygen. Sterilized air or oxygen is a preferred imaging contrast agent.

C. Atomization of polymer solution into a crosslinking solution.

There are at least two methods for the preparation of injectable microcapsules. In one method, a jet head is used that allows the co-extrusion of a solution of polymer and air to produce nascent microencapsulated air bubbles which fall into a hardening solution of counterions. A second method employs ultrasound to introduce cavitation-induced bubbles into the polymer before capsule formation by spraying. To incorporate gases other than air, a solution of the desired polymer is placed in an atmosphere of the desired gas and sonicated for a sufficient amount of time before crosslinking to ensure that gas bubbles are dispersed throughout the microparticulates. In either case, the determining factors on size of resulting microcapsules will be the selection and concentration of polymer and solvent, and size of droplets formed by the atomizer.

1. Preparation of one to ten micron Microcapsules

An example of an air-atomizing device is a Turbotak, from Turbotak, Inc., Waterloo, Ontario. A Turbotak is a hollow stainless steel cylinder, 2.64 cm. wide×4 cm. long. Liquid is fed into the Turbotak from the top and pressurized air is fed from the side. The pressurized air mixes with the liquid, forcing tiny liquid droplets out through the orifice of the nozzle. The air pressure can be set to between 50 and 80 psig. The distance between the orifice of the Turbotak and the pan containing the crosslinking ions is fixed at between about one to two feet. The size of the nozzle orifice is 1 to 2 mm in diameter.

Air can be pressurized with a syringe pump such as a Razel pump, having a flow rate in the range of between 5 ml/hr and 30 ml/hr or a Sage pump, having a flow rate in the range of between 0.02 ml/min and 126 ml/min.

Mixing pressurized air with a polymer solution aerates the polymer solution and produces a high yield of air-encapsulated polymeric microcapsules. Even without sonicating the polymer solution, microcapsules produced using the Turbotak nozzle have entrapped air, as seen by light microscopy.

2. Method for the Preparation of larger Microcapsules

Larger microcapsules can be prepared using a droplet-forming apparatus by spraying an aqueous solution of polymer containing the gas of interest through an apparatus such as a plastic syringe, where the polymer solution is extruded through a needle located inside a tube through which air flows at a controlled rate.

The rate of polymer extrusion is controlled, for example, by a syringe pump. Droplets forming at the needle tip are forced off by the coaxial air stream and collected in the crosslinking solution, usually an aqueous solution of bi- or trivalent ions, where they cross-link and are hardened, for example, for between 15 and 30 minutes.

The shape and size of these microcapsules depend on the polymer and cross-linker concentrations and parameters such as the polymer extrusion rate, air flow, and needle diameters used in the microencapsulation procedure.

A typical example for microcapsule preparation utilizes a polyphosphazene concentration of between 1 and 5% (w/v), preferably around 2.5%, and calcium chloride concentrations of between 3 and 7.5% (w/v), preferably 7.5%, respectively. Polymer extrusion rates are between 50 and 100 mL/hour, preferably 70 mL/hour. Air flow rates are in the range of 5 L/hour. Needle diameters of between 18 and 26 gauge (G), preferably around 20 gauge, are used. Using the preferred conditions, the resultant microcapsules are spherical with diameters in the range of 400–700 microns. In general, microcapsules as small as 30 μM can be prepared using this technique.

Macrospheres with millimeter diameters can be prepared by extruding the polymer through pasteur pipers or their equivalent.

D. Processing the polymeric microcapsules to liquify the core

The polyionic-coated hydrogel microcapsules are collected and further treated with buffer to remove the uncomplexed multivalent ions. For example, to remove uncomplexed multivalent cations, microcapsules can be treated with 0.9% (w/v) KCl with the pH adjusted to around 8.0. The KCl solution dissolves the internal gel, without affecting the external membrane. Other methods can also be used to liquefy the internal gel, including using chelators such as EDTA and sodium citrate.

Microbubbles can be prepared by sonicating solutions of synthetic polymer (typically using ultrasonic frequencies of between 5,000 and 30,000 Hz) to produce a highly aerated gassed solution, and spraying the polymer solution into a solution of multi-valent ions. Microbubbles produced by this method are typically smaller than 7 μm. In fact, the yield of microbubbles after one passage through a 7 μm spectrum filter (polyester-based filter, Spectrum) using this technique can exceed 90%.

Modifications and variations of the present invention will be obvious to those skilled in the art from the foregoing detailed description of the invention. Such modifications and variations are intended to come within the scope of the appended claims.

We claim:

1. A polyphosphazene having a substituent group selected from the group consisting of a chalcone and a cinnamate.

2. The polyphosphazene according to claim 1 further having a substituent group that is ionically crosslinkable.

3. The polyphosphazene according to claim 1 further having a substituent group selected from the group consisting of aliphatic, aryl, aralkyl, alkaryl, amino acid, amino acid ester, carboxylic acid, heteroaromatic, carbohydrate, heteroalkyl, halogen, (aliphatic)amino-, heteroaralkyl, di(aliphatic)amino-, arylamino-, diarylamino-, alkylarylamino-, -oxyaryl, -oxyaliphatic, -oxy(aliphatic)hydroxyl, -oxyalkaryl, -oxyaralkyl, -thioaryl, -thioaliphatic, organosilicon, -NHC(O)O-(aryl or aliphatic), —O—([(alkyl)O]$_x$—CH$_2$)$_y$NH$_2$, wherein the alkyl group can vary within the moiety, —O—[(CH$_2$)$_x$O]$_y$CH$_2$)$_x$NH(CH$_2$)$_x$SO$_3$H, and —O—[(alkyl)—O]$_y$—(aryl or aliphatic), wherein the alkyl group can vary within the moiety, wherein x is 1–8 (which can vary within the moiety) and y is an integer between 1 and 40.

4. The polyphosphazene according to claim 1 wherein the polyphosphazene is prepared from a cyclic phosphazene trimer having a chalcone or cinnamate pendant group.

5. The polyphosphazene according to claim 4 wherein the trimer is selected from the group consisting of $N_3P_3Cl_5\{OC_6H_4CH=CHC(O)C_6H_5\}$, $N_3P_3(OC_6H_5)_5\{OC_6H_4CH=CHC(O)C_6H_5\}$, $N_3P_3\{OCH_2CF_3\}_5\{OCH=CHC(O)C_6H_5\}$, $]NP;55\ OC_6H_4CH=CHC(O)C_6H_5]_2]_3$, $N_3P_3Cl_5(OCH_2CH_2)_2OTHP$, $N_3P_3(OCH_2CF_3)\{(OCH_2CH_2)_2OTHP\}$, $N_3P_3(OCH_2CF_3)_5\{(OCH_2CH_2)_2OH\}$, $N_3P_3(OCH_2CF_3)_5\{(OCH_2CH_2)_2OC(O)CH=CHPh\}$, $N_3P_3Cl_5\{OC_6H_4p\text{-}OBz\}$, $N_3P_3(OCH_2CF_3)_5\{OC_6H_4\text{-}p\text{-}OBz\}$, $[NP(OC_6H_4p\text{-}OBz)_2]_3$, $[NP(OC_6H_4p\text{-}OH)_2]_3$, $[NP(OC_6H_4p\text{-}OC(O)CH=CHPh)_2]_3$, $[NP\{OCH_2CH_2)_2OTHP\}_2]_3$, $[NP\{OCH_2CH_2)_2OH\}_2]_3$, and $[NP\{OCH_2CH_2)_2OC(O)CH=CHPh\}_2]_3$.

6. The polyphosphazene of claim 1, wherein the polyphosphazene is selected from the group consisting of $[NP\{OC_6H_4CH=CHC(O)C_6H_5\}_2]_n$, $[NP\{OC_6H_5\}_1\{OC_6H_4\text{—}CH=CHO(O)C_6H_5\}_1]_n$, and $[NP\{OCH_2CF_3\}_{0.93}\{OC_6H_4CH=CHC(O)C_6H_5\}_{1.07}]n$, wherein n is between 10 and 30,000.

7. The polyphosphazene of claim 6, wherein n is between 1000 and 20,000.

8. The polyphosphazene of claim 1 that is crosslinked.

9. The polyphosphazene of claim 8 which is crosslinked by exposure to radiation.

10. The polyphosphazene of claim 9 wherein the radiation is UV radiation.

11. The polyphosphazene of claim 8 in the form of a microparticle.

12. The polyphosphazene of claim 11 further comprising an imaging contrast agent.

13. The polyphosphazene of claim 12 wherein the imaging contrast agent is a gas selected from the group consisting of air, argon, nitrogen, carbon dioxide, nitrogen dioxide, methane, helium, neon, and oxygen.

14. The polyphosphazene of claim 13 wherein the imaging contrast agent is sterilized air or oxygen.

15. The polyphosphazene of claim 11 further comprising a biologically active material.

16. The polyphosphazene of claim 15 wherein the biological material is selected from the group consisting of proteins, carbohydrates, polysaccharides, nucleic acids, lipids, synthetic molecules, liposomes, viruses, procaryotic cells, eucaryotic cells and combinations thereof.

17. The polyphosphazene of claim 11 having a poly(alkylene glycol) moiety covalently bound to the surface of the microparticle.

18. The polyphosphazene of claim 1 wherein the polyphosphazene has both phenoxycarboxylato and photocrosslinkable groups.

19. The polyphosphazene of claim 18 wherein the photocrosslinkable group is the chalcone group, and the polyphosphazene is a copolymer having approximately 70, 80 or 90% carboxylato groups and the remaining percentage chalcone groups.

20. The polyphosphazene of claim 19 wherein the polyphosphazene is crosslinked through the carboxylato side groups with di- or trivalent cations.

21. The polyphosphazene of claim 19 wherein the polyphosphazene is stabilized by crosslinking the chalcone groups.

22. The polyphosphazene of claim 18 in which the poly(carboxylatophenoxy)phosphazene is ionically crosslinked to form a hydrogel).

23. The polyphosphazene of claim 1 further having an unsaturated group other than chalcone or cinnamate capable of crosslinking on exposure to UV irradiation.

24. The polyphosphazene of claim 1 further having a substituent group that bears a carboxylic acid, sulfonic acid, hydroxyl, or other ionizable moiety that ionically crosslinks when mixed with a cation selected from the group consisting of zinc, calcium, bismuth, barium, magnesium, aluminum, copper, cobalt, nickel, and cadmium.

25. The polyphosphazene of claim 1 further having a substituent group that is susceptible to hydrolysis under the condition of use.

26. The polyphosphazene of claim 1 further having a substituent group that imparts biodegradability to the polymer.

27. The polyphosphazene of claim 26 wherein the substituent group is selected from the group consisting of chlorine, amino acid, amino acid ester, imidazole, glycerol, and glucosyl.

28. The polyphosphazene of claim 1 further having a pendant poly(alkylene glycol) moiety.

29. The polyphosphazene of claim 28 wherein the terminal hydroxyl group of the poly(alkylene glycol) moiety is covalently attached to a biologically active molecule or a molecule that affects the charge, lipophilicity or hydrophilicity of the particle.

30. The polyphosphazene of claim 11 having a diameter of between approximately one and seven microns.

* * * * *